(12) United States Patent  
Chetham

(10) Patent No.: US 8,594,781 B2  
(45) Date of Patent: Nov. 26, 2013

(54) MONITORING SYSTEM

(75) Inventor: Scott Chetham, Del Mar, CA (US)

(73) Assignee: Impedimed Limited, Pinkenba, Queensland (AU)

( * ) Notice: Subject to any disclaimer, the term of this patent is extended or adjusted under 35 U.S.C. 154(b) by 361 days.

(21) Appl. No.: 12/523,159

(22) PCT Filed: Jan. 14, 2008

(86) PCT No.: PCT/AU2008/000034
§ 371 (c)(1),
(2), (4) Date: Dec. 14, 2009

(87) PCT Pub. No.: WO2008/086565
PCT Pub. Date: Jul. 24, 2008

(65) Prior Publication Data
US 2010/0100003 A1  Apr. 22, 2010

(30) Foreign Application Priority Data

Jan. 15, 2007 (AU) ................................ 2007900175
Nov. 5, 2007 (AU) ................................ 2007906049

(51) Int. Cl.
*A61B 5/00* (2006.01)
(52) U.S. Cl.
USPC ........................................................ 600/547
(58) Field of Classification Search
USPC ........................................................ 600/547
See application file for complete search history.

(56) References Cited

U.S. PATENT DOCUMENTS

| 3,316,896 A | 5/1967 | Thomasset |
| 3,851,641 A | 12/1974 | Toole et al. |
| 3,871,359 A | 3/1975 | Pacela |
| 4,008,712 A | 2/1977 | Nyboer |
| 4,034,854 A | 7/1977 | Bevilacqua |
| 4,144,878 A | 3/1979 | Wheeler |
| 4,184,486 A | 1/1980 | Papa |
| 4,291,708 A | 9/1981 | Frei et al. |

(Continued)

FOREIGN PATENT DOCUMENTS

| CA | 2231038 | 11/1999 |
| CA | 2638958 A1 | 6/2000 |

(Continued)

OTHER PUBLICATIONS

International Preliminary Report on Patentability and Written Opinion of the International Searching Authority dated Mar. 17, 2008 cited in PCT/AU2008/000034.

(Continued)

*Primary Examiner* — Max Hindenburg
(74) *Attorney, Agent, or Firm* — Knobbe Martens Olson & Bear LLP

(57) ABSTRACT

A method for performing impedance measurements on a subject. The method includes, in a processing system, causing at least one electrical signal to be applied to the subject via first leads operatively connected to first electrodes provided on the subject, determining a first indication indicative of at least one first electrical signal measured via second leads operatively disconnected from second electrodes positioned on the subject, determining a second indication indicative of at least one second electrical signal measured via second leads operatively connected to second electrodes positioned on the subject, and determining from the indications and the at least one applied signal, at least one instantaneous impedance value.

20 Claims, 16 Drawing Sheets

(56) References Cited

U.S. PATENT DOCUMENTS

| | | |
|---|---|---|
| 4,314,563 A | 2/1982 | Wheeler |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,468,832 A | 9/1984 | Batchelor |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,895,163 A | 1/1990 | Libke et al. |
| 4,905,705 A | 3/1990 | Kizakevich et al. |
| 4,911,175 A | 3/1990 | Shizgal |
| 4,942,880 A | 7/1990 | Slovák |
| 4,951,682 A | 8/1990 | Petre |
| 5,025,784 A | 6/1991 | Shao et al. |
| 5,063,937 A | 11/1991 | Ezenwa et al. |
| 5,143,079 A | 9/1992 | Frei et al. |
| 5,197,479 A | 3/1993 | Hubelbank et al. |
| 5,246,008 A | 9/1993 | Mueller |
| 5,280,429 A | 1/1994 | Withers |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel |
| 5,449,000 A | 9/1995 | Libke et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,544,662 A | 8/1996 | Saulnier et al. |
| 5,588,429 A | 12/1996 | Isaacson et al. |
| 5,704,355 A | 1/1998 | Bridges |
| 5,732,710 A | 3/1998 | Rabinovich et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,919,142 A | 7/1999 | Boone et al. |
| 6,011,992 A | 1/2000 | Hubbard et al. |
| 6,015,389 A | 1/2000 | Brown |
| 6,018,677 A | 1/2000 | Vidrine et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Ferrer et al. |
| 6,173,003 B1 | 1/2001 | Whikehart et al. |
| 6,228,022 B1 | 5/2001 | Friesem et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,496,725 B2 | 12/2002 | Kamada et al. |
| 6,497,659 B1 | 12/2002 | Rafert |
| 6,532,384 B1 | 3/2003 | Fukuda |
| 6,560,480 B1 | 5/2003 | Nachaliel et al. |
| 6,569,160 B1 | 5/2003 | Goldin et al. |
| 6,584,348 B2 | 6/2003 | Glukhovsky |
| 6,618,616 B2 | 9/2003 | Iijima et al. |
| 6,625,487 B2 | 9/2003 | Herleikson |
| 6,631,292 B1 | 10/2003 | Liedtke |
| 6,633,777 B2 | 10/2003 | Szopinski |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,760,617 B2 | 7/2004 | Ward et al. |
| 6,768,921 B2 | 7/2004 | Organ et al. |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 7,130,680 B2 | 10/2006 | Kodama et al. |
| 7,148,701 B2 | 12/2006 | Park et al. |
| 7,212,852 B2 | 5/2007 | Smith et al. |
| 7,457,660 B2 | 11/2008 | Smith et al. |
| 7,477,937 B2 | 1/2009 | Iijima et al. |
| 7,706,872 B2 | 4/2010 | Min et al. |
| 7,733,224 B2 | 6/2010 | Tran |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2002/0020138 A1 | 2/2002 | Walker et al. |
| 2002/0022787 A1 | 2/2002 | Takehara et al. |
| 2002/0072686 A1 | 6/2002 | Hoey et al. |
| 2002/0079910 A1 | 6/2002 | Fukuda |
| 2002/0093991 A1 | 7/2002 | Kurihara et al. |
| 2002/0093992 A1 | 7/2002 | Plangger |
| 2002/0109621 A1 | 8/2002 | Khair et al. |
| 2002/0123694 A1 | 9/2002 | Organ et al. |
| 2002/0161311 A1 | 10/2002 | Ward et al. |
| 2002/0194419 A1 | 12/2002 | Rajput et al. |
| 2003/0004403 A1 | 1/2003 | Drinan et al. |
| 2003/0023184 A1 | 1/2003 | Pitts-Crick et al. |
| 2003/0028221 A1 | 2/2003 | Zhu et al. |
| 2003/0050570 A1 | 3/2003 | Kodama et al. |
| 2003/0073916 A1 | 4/2003 | Yonce |
| 2003/0105411 A1 | 6/2003 | Smallwood et al. |
| 2003/0120170 A1 | 6/2003 | Zhu et al. |
| 2004/0015095 A1 | 1/2004 | Li et al. |
| 2004/0019292 A1 | 1/2004 | Drinan et al. |
| 2004/0077944 A1 | 4/2004 | Steinberg et al. |
| 2004/0158167 A1 | 8/2004 | Smith et al. |
| 2004/0167423 A1 | 8/2004 | Pillon et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0252870 A1 | 12/2004 | Reeves et al. |
| 2004/0253652 A1 | 12/2004 | Davies |
| 2004/0267344 A1 | 12/2004 | Stett et al. |
| 2005/0033281 A1 | 2/2005 | Bowman et al. |
| 2005/0039763 A1 | 2/2005 | Kraemer et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0203435 A1 | 9/2005 | Nakada |
| 2005/0261743 A1 | 11/2005 | Kroll |
| 2006/0004300 A1 | 1/2006 | Kennedy |
| 2006/0085048 A1 | 4/2006 | Cory et al. |
| 2006/0085049 A1 | 4/2006 | Cory et al. |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0224079 A1 | 10/2006 | Washchuk |
| 2006/0224080 A1 | 10/2006 | Oku et al. |
| 2006/0264775 A1 | 11/2006 | Mills et al. |
| 2006/0270942 A1 | 11/2006 | McAdams |
| 2007/0010758 A1 | 1/2007 | Matthiessen et al. |

(56) References Cited

U.S. PATENT DOCUMENTS

| | | |
|---|---|---|
| 2007/0027402 A1 | 2/2007 | Levin et al. |
| 2007/0043303 A1* | 2/2007 | Osypka et al. ............ 600/547 |
| 2007/0087703 A1 | 4/2007 | Li et al. |
| 2007/0106342 A1 | 5/2007 | Schumann |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0039700 A1 | 2/2008 | Drinan et al. |
| 2008/0188757 A1 | 8/2008 | Rovira et al. |
| 2008/0205717 A1 | 8/2008 | Reeves et al. |
| 2008/0319336 A1 | 12/2008 | Ward et al. |
| 2009/0043222 A1 | 2/2009 | Chetham |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0287102 A1 | 11/2009 | Ward |
| 2009/0318778 A1 | 12/2009 | Dacso et al. |
| 2010/0168530 A1 | 7/2010 | Chetham et al. |
| 2011/0118619 A1 | 5/2011 | Burton et al. |

FOREIGN PATENT DOCUMENTS

| | | |
|---|---|---|
| CA | 2613524 | 1/2007 |
| CA | 2615845 | 1/2007 |
| DE | 2912349 | 10/1980 |
| EP | 0249823 | 12/1987 |
| EP | 349043 | 3/1990 |
| EP | 0357309 | 3/1990 |
| EP | 377887 | 7/1990 |
| EP | 339471 | 3/1997 |
| EP | 865763 | 9/1998 |
| EP | 0869360 | 10/1998 |
| EP | 1112715 | 4/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1338246 | 8/2003 |
| EP | 1452131 | 9/2004 |
| EP | 1553871 | 7/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| FR | 2486386 | 1/1982 |
| FR | 2748928 | 11/1997 |
| GB | 2131558 | 6/1984 |
| GB | 2260416 | 4/1993 |
| GB | 2426824 | 12/2006 |
| IT | 20080030 | 1/2010 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 10-225521 | 8/1998 |
| JP | 11070090 | 3/1999 |
| JP | 2000107138 | 4/2000 |
| JP | 2000139867 | 5/2000 |
| JP | 2001-224568 A | 8/2001 |
| JP | 2001321352 | 11/2001 |
| JP | 2002330938 | 11/2002 |
| JP | 2003116805 | 4/2003 |
| JP | 2003-230547 A | 8/2003 |
| JP | 2004-61251 A | 2/2004 |
| JP | 2008022995 | 7/2008 |
| RU | 2112416 | 6/1998 |
| WO | WO 88/07392 | 10/1988 |
| WO | WO 93/18821 | 9/1993 |
| WO | WO 96/01586 | 1/1996 |
| WO | WO 96/12439 | 5/1996 |
| WO | WO 96/32652 | 10/1996 |
| WO | WO 97/11638 | 4/1997 |
| WO | WO 97/14358 | 4/1997 |
| WO | WO 98/06328 | 2/1998 |
| WO | WO 98/23204 | 6/1998 |
| WO | WO 98/33553 | 8/1998 |
| WO | WO 00/40955 | 7/2000 |
| WO | WO 00/79255 | 12/2000 |
| WO | WO 01/50954 | 7/2001 |
| WO | WO 01/67098 | 9/2001 |
| WO | 02-53028 A2 | 7/2002 |
| WO | WO 02/062214 | 8/2002 |
| WO | WO 02/094096 | 11/2002 |
| WO | WO 04/000115 | 12/2003 |
| WO | 2004-032738 A1 | 4/2004 |
| WO | WO 2004/026136 | 4/2004 |
| WO | 2004-043252 A1 | 5/2004 |
| WO | 2004-047636 A1 | 6/2004 |
| WO | WO 2004/047635 | 6/2004 |
| WO | WO 2004/047638 | 6/2004 |
| WO | WO 2004/049936 | 6/2004 |
| WO | WO 2004/083804 | 9/2004 |
| WO | 2004-098389 A2 | 11/2004 |
| WO | WO 2005/010640 | 2/2005 |
| WO | WO 2005/027717 | 3/2005 |
| WO | WO 2005/051194 | 6/2005 |
| WO | WO 2005/122888 | 12/2005 |
| WO | WO 2006/129108 | 12/2006 |
| WO | WO 2006/129116 | 12/2006 |
| WO | WO 2007/002991 | 1/2007 |
| WO | WO 2007/002992 | 1/2007 |
| WO | WO 2007/002993 | 1/2007 |
| WO | WO 2007/009183 | 1/2007 |
| WO | WO 2007/041783 | 4/2007 |
| WO | 2007-056493 A1 | 5/2007 |
| WO | WO 2008/064426 | 6/2008 |
| WO | WO 2008/138062 | 11/2008 |
| WO | WO 2009/036369 | 3/2009 |
| WO | WO 2009/100491 | 8/2009 |
| WO | WO 2011/022068 | 2/2011 |
| WO | WO 2011/050393 | 5/2011 |
| WO | WO 2011/075769 | 6/2011 |

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.

Al-Hatib, F.; Patient Instrument connection errors in bioelectrical impedance measurement; Physiological Measurement; vol. 19, No. 2, pp. 285-296; May 2, 1998.

Boulier, A. et al.; Fat-Free Mass Estimation by Two Electrode Impedance Method; American Journal of Clinical Nutrition; vol. 52, pp. 581-585; 1990.

Bracco, D. et al., Bedside determination of fluid accumulation after cardiac surgery using segmental bioelectrical impedance, Critical Care Medicine, vol. 26, No. 6, pp. 1065-1070, 1998.

Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.

Chiolero, R.L. et al.; Assessment of changes in body water by bioimpedance in acutely ill surgical patients; Intensive Care Medicine; vol. 18, pp. 322-326; 1992.

Chumlea et al.; Bioelectrical Impedance and Body Composition: Present Status and Future Directions; Nutrition Reviews; vol. 52, No. 4, pp. 123-131; 1994.

Cornish, B.H. et al.; Alteration of the extracellular and total body water volumes measured by multiple frequency bioelectrical impedance analysis; Nutrition Research; vol. 14, No. 5, pp. 717-727; 1994.

Cornish, B.H. et al.; Bioelectrical impedance for monitoring the efficacy of lymphoedema treatment programmes; Breast Cancer Research and Treatment; vol. 38, pp. 169-176; 1996.

(56) References Cited

OTHER PUBLICATIONS

Cornish, B.H. et al.; Data analysis in multiple-frequency bioelectrical impedance analysis; Physiological Measurement; vol. 19, No. 2, pp. 275-283; May 1, 1998.
Cornish, B.H. et al.; Early diagnosis of lymphedema using multiple frequency bioimpedance; Lymphology; vol. 34, pp. 2-11; Mar. 2001.
Cornish, B.H. et al.; Early diagnosis of lymphoedema in postsurgery breast cancer patients; Annals New York Academy of Sciences; pp. 571-575; May 2000.
Cornish, B.H. et al.; Quantification of Lymphoedema using Multi-frequency Bioimpedance; Applied Radiation and Isotopes; vol. 49, No. 5/6, pp. 651-652; 1998.
De Luca, F. et al., Use of low-frequency electrical impedance measurements to determine phospoholipid content in amniotic fluid; Physics in Medicine and Biology, vol. 41, pp. 1863-1869, 1996.
Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.
Dines K.A. et al.; Analysis of electrical conductivity imaging; Geophysics; vol. 46, No. 7, pp. 1025-1036; Jul. 1981.
Ellis, , K.J. et al: Human hydrometry: comparison of multifrequency bioelectrical impedance with 2H2O and bromine dilution; Journal of Applied Physiology; vol. 85, No. 3, pp. 1056-1062; 1998.
Forslund, A.H. et al.; Evaluation of modified multicompartment models to calculate body composition in healthy males; American Journal of Clinical Nutrition; vol. 63, pp. 856-62; 1996.
Gersing, E.; Impedance spectroscopy on living tissue for determination of the state of Organs; Bioelectrochemistry and Bioenergetics; vol. 45, pp. 145-149; 1998.
Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. At Chapel Hill; pp. 446-453; Jun. 1990.
Gudivaka R. et al; Single- and multifrequency models for bioelectrical impedance analysis of body water compartments; Applied Physiology; vol. 87, Issue 3, pp. 1087-1096; 1999.
Jones, C.H. et al; Extracellular fluid volume determined by bioelectric impedance and serum albumin in CAPD patients; Nephrology Dialysis Transplantation; vol. 13, pp. 393-397; 1998.
Jossinet, J. et al.; A Study for Breast Imaging with a Circular Array of Impedance Electrodes; Proc. Vth Int. Conf. Bioelectrical Impedance, 1981, Tokyo, Japan; pp. 83-86; 1981.
Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.
Kanai, H. et al.; Electrical Measurement of Fluid Distribution in Legs and Arms; Medical Progress through technology; pp. 159-170; 1987.
Kim, C.T. et al.; Bioelectrical impedance changes in regional extracellular fluid alterations; Electromyography and Clinical Neurophysiology; vol. 37, pp. 297-304; 1997.
Liu R. et al; Primary Multi-frequency Data Analyze in Electrical Impedance Scanning; Proceedings of the IEEE-EMBS 2005, 27th Annual International Conference of the Engineering in Medicine and Biology Society, Shanghai, China; pp. 1504-1507; Sep. 1-4, 2005.
Lozano, A. et al.; Two-frequency impedance plethysmograph: real and imaginary parts; Medical & Biological Engineering & Computing; vol. 28, No. 1, pp. 38-42; Jan. 1990.
Lukaski, H.C. et al.; Estimation of Body Fluid Volumes Using Tetrapolar Bioelectrical Impedance Measurements; Aviation, Space, and Environmental Medicine; pp. 1163-1169; Dec. 1998.
Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.

Mattar, J.A., Application of Total Body Impedance to the Critically Ill Patient, New Horizons, vol. 4, No. 4, pp. 493-503, 1996.
McDougal D., et al.; Body Composition Measurements From Whole Body Resistance and Reactance; Surgical Forum; vol. 36, pp. 43-44; 1986.
Osterman K.S. et al.; Multifrequency electrical impedance imaging: preliminary in vivo experience in breast; Physiological Measurement; vol. 21, No. 1, pp. 99-109; Feb. 2000.
Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.
Pethig, R. et al.; The Passive Electrical Properties of Biological Systems: Their Significance In Physiology, Biophysics and Biotechnology; Physics in Medicine and Biology; vol. 32, pp. 933-970; 1987.
Piperno, G. et al.; Breast Cancer Screening by Impedance Measurements; Frontiers of Medical & Biological Engineering; vol. 2, pp. 111-117; 1990.
Rigaud, B. et al.; Bioelectrical Impedance Techniques in Medicine; Critical Reviews in Biomedical Engineering; vol. 24 (4-6), pp. 257-351; 1996.
Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.
Skidmore, R. et al.; A Data Collection System for Gathering Electrical Impedance Measurements from the Human Breast; Clinical Physics Physiological Measurement; vol. 8, pp. 99-102; 1987.
Sollish, B.D. et al.; Microprocessor-assisted Screening Techniques; Israel Journal of Medical Sciences; vol. 17, pp. 859-864; 1981.
Steijaert, M. et al.; The use of multi-frequency impedance to determine total body water and extracellular water in obese and lean female individuals; International Journal of Obesity; vol. 21, pp. 930-934; 1997.
Surowiec, A.J. et al.; Dielectric Properties of Brest Carcinoma and the Surrounding Tissues; IEEE Transactions on Biomedical Engineering; vol. 35, pp. 257-263; 1988.
Tedner, B.; Equipment Using Impedance Technique for Automatic Recording of Fluid-Volume Changes During Haemodialysis; Medical & Biological Engineering & Computing; pp. 285-290; 1983.
Thomas. B.J. et al.; Bioelectrical impedance analysis for measurement of body fluid volumes—A review; Journal of Clinical Engineering; vol. 17, No. 16, pp. 505-510; 1992.
Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.
Thomas. B.J.; Future Technologies; Asia Pacific Journal Clinical Nutrition; vol. 4, pp. 157-159; 1995.
Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.
Ward, L.C. et al., Multi-frequency bioelectrical impedance augments the diagnosis and management of lymphoedema in post-mastectomy patients, European Journal of Clinical Investigation, vol. 22, pp. 751-754, 1992.
Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.
Ward, L.C. et al.; There is a better way to measure Lymphoedema; National Lymphedema Network Newsletter; vol. 7, No. 4, pp. 89-92; Oct. 1995.
Woodrow, G. et al; Effects of icodextrin in automated peritoneal dialysis on blood pressure and bioelectrical impedance analysis; Nephrology Dialysis Transplantation; vol. 15, pp. 862-866; 2000.

(56) References Cited

OTHER PUBLICATIONS

Iacobellis, G., et al. Influence Of Excess Fat On Cardiac Morphology And Function: Study In Uncomplicated Obesity, (2002) Obesity Research, vol. 10, pp. 767-773, Aug. 8, 2002.

Bella, et al., Relations Of Left Ventricular Mass To Fat-Free And Adipose Body Mass: The Strong Heart Study, (1998) Circulation, vol. 98, pp. 2538-2544.

Karason, K., et al., Impact Of Blood Pressure And Insulin On The Relationship Between Body Fat And Left Ventricular Structure, (2003) European Heart Journal, vol. 24, pp. 1500-1505.

Yoshinaga, M., Effect Of Total Adipose Weight And Systemic Hypertension On Left Ventricular Mass In Children, American Journal of Cardiology, (1995) vol. 76, pp. 785-787.

* cited by examiner

MONITORING SYSTEM

BACKGROUND OF THE INVENTION

The present invention relates to a method and apparatus for performing impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological parameters relating to a subject involves the use of bioelectrical impedance. This involves applying electrical signals to a subject and then measuring signals induced within the subject, using a series of electrodes placed on the skin surface, allowing the electrical impedance of the subject's body to be determined. This information can then be used to derive parameters indicative of fluid levels within the subject.

Typical impedance measuring devices operate by applying electrical signals, such as current signals, to the subject via first leads, with induced signals, such as voltage signals, being measured via second leads. The induced signals typically have a small magnitude, and accordingly it is necessary to ensure that noise and other interference within the impedance measuring apparatus is minimised.

In such arrangements, one source of noise results from inductive coupling between the first and second leads. This is caused by the generation of a changing magnetic field within the first leads, which in turn induces a current in the second leads. This induced current interferes with the measurement of the induced voltage, which can in turn impact on the accuracy of the impedance measurement process.

Other external factors that can impact on impedance measurements can include stray capacitances between the subject and the local environment and the measurement apparatus, variations in electrode/tissue interface impedances, also known as electrode impedances, as well as stray capacitances between the leads used to connect the measuring device to the electrodes.

SUMMARY OF THE PRESENT INVENTION

In a first broad form the present invention provides a method for performing impedance measurements on a subject, the method including, in a processing system:
a) causing at least one electrical signal to be applied to the subject via first leads operatively connected to first electrodes provided on the subject;
b) determining a first indication indicative of at least one first electrical signal measured via second leads operatively disconnected from second electrodes positioned on the subject;
c) determining a second indication indicative of at least one second electrical signal measured via second leads operatively connected to second electrodes positioned on the subject; and,
d) determining from the indications and the at least one applied signal, at least one instantaneous impedance value.

Typically the second leads are connected to the second electrodes via respective switches, and wherein the method includes, in the processing system, causing the switches to be selectively opened and closed to allow the first and second indications to be determined.

Typically the method includes, in the processing system:
a) opening the switches;
b) determining the first indication;
c) closing the switches; and,
d) determining the second indication.

Typically each second lead includes a lead pair, and wherein each lead pair includes a lead operatively connected to the second electrodes and a lead operatively disconnected to the second electrodes, and wherein the method includes, in the processing system:
a) determining the first indication using the lead operatively disconnected to the second electrodes; and,
b) determining the second indication using the lead operatively connected to the second electrodes.

Typically the method includes, in the processing system:
a) determining a number of frequencies;
b) selecting a next frequency from the number of frequencies;
c) causing the at least one electrical signal to be applied to the subject at the selected frequency;
d) determining the first and second indications; and,
e) repeating steps (b), (c) and (d) for each of the number of frequencies.

Typically the method includes, in the processing system:
a) determining at least one impedance measurement to be performed; and,
b) determining the number of frequencies using the determined impedance measurement.

Typically the method includes, in the processing system:
a) determining an indication of the at least one signal applied to the subject; and,
b) determining the at least one instantaneous impedance value using the determined indication.

Typically the method includes, in the processing system:
a) modifying the second indication using the first indication; and,
b) using the modified second indication to determine the at least one instantaneous impedance value.

Typically the method includes, in the processing system:
a) determining at least one first instantaneous impedance value using the first indication;
b) determining at least one second instantaneous impedance value using the second indication; and,
c) determining the at least one instantaneous impedance value using the first and second instantaneous impedance values.

Typically the method includes, in the processing system, using the first and second indications to account for inductive coupling between the first and second leads.

In a second broad form the present invention provides apparatus for performing impedance measurements on a subject, the apparatus including, a processing system for:
a) causing at least one electrical signal to be applied to the subject via first leads operatively connected to first electrodes provided on the subject;
b) determining a first indication indicative of at least one first electrical signal measured via second leads operatively disconnected from second electrodes positioned on the subject;
c) determining a second indication indicative of at least one second electrical signal measured via second leads operatively connected to second electrodes positioned on the subject; and, d) determining from the indications and the at least one applied signal, at least one instantaneous impedance value.

Typically the apparatus includes switches for selectively operatively connecting the second electrodes to the second leads.

Typically the processing system is for opening and closing the switches to thereby selectively operatively connect the second electrodes to the second leads.

Typically the apparatus includes buffer circuits for coupling the second leads to the second electrodes.

Typically the apparatus includes switches positioned between the buffer circuits and the second electrodes for selectively operatively connecting the second leads to the second electrodes.

Typically each second lead includes a lead pair, and wherein each lead pair includes a lead operatively connected to the second electrodes and a lead operatively disconnected to the second electrodes.

In a third broad form the present invention provides a method for use in performing impedance measurements on a subject, wherein the method includes, in a processing system:
 a) causing a first signal to be applied to the subject;
 b) determining an indication of a second signal measured across the subject;
 c) using the indication of the second signal to determine any imbalance;
 d) determining a modified first signal in accordance with the imbalance;
 e) causing the modified first signal to be applied to the subject to thereby allow at least one impedance measurement to be performed.

Typically the second signal is a voltage sensed at respective second electrodes and wherein the method includes, in the processing system:
 a) determining the voltage sensed at each of the second electrodes;
 b) determining a first voltage using the voltage sensed at each of the second electrodes; and,
 c) determining the imbalance using the first voltage.

Typically the first voltage is a common mode signal.

Typically the method includes, in the processing system, determining the modified first signal so as to minimise the imbalance.

Typically the first signal is a voltage applied to the subject using the first electrodes and the second signal is a voltage sensed at respective second electrodes, and wherein the method includes, in the processing system, performing the impedance measurement by:
 a) determining a current flow caused by applying the first signal to the subject;
 b) determining the voltage sensed at each of the second electrodes;
 c) determining a second voltage using the voltage sensed at each of the second electrodes;
 d) determining an impedance parameter using the determined current flow and the second voltage.

Typically the second voltage is a differential voltage.

Typically the first signal is a voltage applied to the subject using the first electrodes, and wherein the method includes, in the processing system, performing the impedance measurement by:
 a) determining a current flow caused by applying the first signal to the subject;
 b) comparing the current flow to a threshold; and,
 c) selectively halting application of the first signal to the subject depending on the results of the comparison.

Typically the method includes, in the processing system, performing impedance measurements at each of a number of frequencies by:
 a) causing a first signal to be applied to the subject at a first frequency;
 b) determining an indication of a second signal measured across the subject;
 c) using the indication of the second signal to determine an imbalance;
 d) determining a modified first signal in accordance with the imbalance;
 e) causing the modified first signal to be applied to the subject to thereby allow at least one impedance measurement to be performed at the first frequency; and,
 f) repeating steps a) to e) for at least one second frequency.

Typically the method includes, in the processing system:
 a) generating control signals, the control signals being used to apply one or more signals to the subject;
 b) receiving an indication of the one or more signals applied to the subject;
 c) receiving an indication of one or more signals measured across the subject; and,
 d) performing at least preliminary processing of the indications to thereby allow impedance values to be determined.

In a fourth broad form the present invention provides apparatus for performing impedance measurements, the apparatus including a processing system for:
 a) causing a first signal to be applied to the subject;
 b) determining an indication of a second signal measured across the subject;
 c) using the indication of the second signal to determine an imbalance;
 d) determining a modified first signal in accordance with the imbalance;
 e) causing the modified first signal to be applied to the subject to thereby allow at least one impedance measurement to be performed.

Typically the processing system is for:
 a) generating control signals, the control signals being used to apply one or more signals to the subject;
 b) receiving an indication of the one or more signals applied to the subject;
 c) receiving an indication of one or more signals measured across the subject; and,
 d) performing at least preliminary processing of the indications to thereby allow impedance values to be determined.

Typically the apparatus includes at least one signal generator for:
 a) receiving one or more control signals;
 b) amplifying the control signals to thereby generate the first signal;
 c) applying the first signal to the subject via a first electrode; and,
 d) providing an indication of a parameter relating to the first signal applied to the subject.

Typically the apparatus includes a respective signal generator for each first electrode.

Typically the first signal is a voltage, and wherein the signal generator is for providing an indication of the current flow through the subject.

Typically the apparatus includes at least one sensor for measuring the second signals via second electrodes.

Typically the apparatus includes a respective sensor for each second electrode.

Typically the apparatus includes a differential amplifier for amplifying second signals measured at each of two second electrodes.

Typically the differential amplifier generates at least one of:
   a) a differential voltage indicative of the voltage measured at the second electrodes; and,
   b) a common mode signal indicative of any imbalance.

Typically the apparatus includes an electrode system including:
   a) a first substrate having the signal generator and sensor mounted thereon; and,
   b) a second substrate having at least two conductive pads mounted thereon, the conductive pads being for coupling the signal generator and the sensor to a subject in use.

Typically the apparatus includes at least one lead for at least partially connecting a measuring device to first and second electrodes, the lead including:
   a) at least two connections for connecting the measuring device and the signal generator, and the measuring device and the sensor; and,
   b) a shield for each of the at least two connections, the shields being electrically connected, and connected to a reference potential in each of the measuring device and the electrode system.

Typically the apparatus includes:
   a) at least two electrode systems, each electrode system including:
      i) a signal generator for applying a first signal to be applied to the subject;
      ii) a sensor for sensing a second signal across the subject;
      iii) a first electrode for coupling the signal generator to the subject; and,
      iv) a second electrode for coupling the sensor to the subject; and,
   b) a measuring device for controlling the electrode systems to allow impedance measurements to be performed; and,
   c) at least two leads for connecting the measuring device to the electrode systems, the leads being arranged to at least one of:
      i) extend from the measuring device in different directions to thereby reduce inductive coupling therebetween; and,
      ii) minimise the lead length.

Typically the apparatus includes an interface for coupling the processing system to a computer system, the processing system being for:
   a) generating control signals in accordance with commands received from the computer system; and,
   b) providing data indicative of measured impedance values to the computer system to allow impedance values to be determined.

Typically the processing system is an FPGA.

Typically the computer system is for:
   a) generating commands for controlling the processing system;
   b) receiving data indicative of measured impedance values from the processing system; and,
   c) determining impedance values using the data.

In a fifth broad form the present invention provides apparatus for use in performing impedance measurements on a subject, wherein the apparatus includes leads for connecting a measuring device to an electrode system, the electrode system including a signal generator and a sensor, the leads including:
   a) at least two connections for connecting the measuring device and the signal generator, and the measuring device and the sensor; and,
   b) a shield for each of the at least two connections, the shields being electrically connected, and connected to a reference potential in each of the measuring device and the electrode system.

Typically the reference potential is a ground potential.

Typically the leads include:
   a) a first cable for coupling the measuring device to the signal generator to thereby allow the measuring device to control the signal generator to apply a first signal to the subject;
   b) a second cable for coupling the measuring device to the signal generator to thereby allow the measuring device to determine a parameter relating to the first signal applied to the subject; and,
   c) a third cable for coupling the measuring device to the sensor generator to thereby allow the measuring device to determine a voltage measured at the subject.

Typically the electrode system includes:
   a) a first substrate having the signal generator and sensor mounted thereon; and,
   b) a second substrate having at least two conductive pads mounted thereon, the conductive pads being for coupling the signal generator and the sensor to a subject in use.

In a sixth broad form the present invention provides apparatus for use in performing impedance measurements on a subject, wherein the apparatus includes:
   a) at least two electrode systems, each electrode system including:
      i) a signal generator for applying a first signal to be applied to the subject;
      ii) a sensor for sensing a second signal across the subject;
      iii) a first electrode for coupling the signal generator to the subject; and,
      iv) a second electrode for coupling the sensor to the subject; and,
   b) a measuring device for controlling the electrode systems to allow impedance measurements to be performed; and,
   c) at least two leads for connecting the measuring device to the electrode systems, the leads being arranged to at least one of:
      i) extend from the measuring device in different directions to thereby reduce inductive coupling therebetween; and,
      ii) minimise the lead length.

Typically the apparatus includes:
   a) four electrode systems; and,
   b) four leads extending from the measuring device in four different directions.

Typically the apparatus includes a support for supporting a subject's limbs to thereby position the measuring device substantially between the subject's knees.

Typically each lead includes:
   a) a first cable for coupling the measuring device to the signal generator to thereby allow the measuring device to control the signal generator to apply a first signal to the subject;
   b) a second cable for coupling the measuring device to the signal generator to thereby allow the measuring device to determine a parameter relating to the first signal applied to the subject; and,
   c) a third cable for coupling the measuring device to the sensor generator to thereby allow the measuring device to determine a voltage measured at the subject.

Typically the electrode system includes:
a) a first substrate having the signal generator and sensor mounted thereon; and,
b) a second substrate having at least two conductive pads mounted thereon, the conductive pads being for coupling the signal generator and the sensor to a subject in use.

In a seventh broad form the present invention provides a method of using apparatus for performing impedance measurements on a subject, wherein the apparatus includes:
a) at least two electrode systems, each electrode system including:
   i) a signal generator for applying a first signal to be applied to the subject;
   ii) a sensor for sensing a second signal across the subject;
   iii) a first electrode for coupling the signal generator to the subject; and,
   iv) a second electrode for coupling the sensor to the subject; and,
b) a measuring device for controlling the electrode systems to allow impedance measurements to be performed; and,
c) at least two leads for connecting the measuring device to the electrode systems, wherein the method includes, arranging the leads to at least one of:
   i) extend from the measuring device in different directions to thereby reduce inductive coupling therebetween; and,
   ii) minimise the lead length.

In an eighth broad form the present invention provides a method for use in determining body composition, the method including, in a processing system:
a) causing a first signal to be applied to the subject;
b) determining an indication of a second signal measured across the subject;
c) using the indication of the second signal to determine any imbalance;
d) determining a modified first signal in accordance with the imbalance;
e) causing the modified first signal to be applied to the subject to thereby allow at least one impedance measurement to be performed.

In a ninth broad form the present invention provides a method of using apparatus for use in determining body composition, wherein the apparatus includes:
a) at least two electrode systems, each electrode system including:
   i) a signal generator for applying a first signal to be applied to the subject;
   ii) a sensor for sensing a second signal across the subject;
   iii) a first electrode for coupling the signal generator to the subject; and,
   iv) a second electrode for coupling the sensor to the subject; and,
b) a measuring device for controlling the electrode systems to allow impedance measurements to be performed; and,
c) at least two leads for connecting the measuring device to the electrode systems, and wherein the method includes, arranging the leads to at least one of:
   i) extend from the measuring device in different directions to thereby reduce inductive coupling therebetween; and,
   ii) minimise the lead length.

In a tenth broad form the present invention provides a method for use in diagnosing the presence, absence or degree of oedema, the method including, in a processing system:
a) causing a first signal to be applied to the subject;
b) determining an indication of a second signal measured across the subject;
c) using the indication of the second signal to determine any imbalance;
d) determining a modified first signal in accordance with the imbalance;
e) causing the modified first signal to be applied to the subject to thereby allow at least one impedance measurement to be performed.

In an eleventh broad form the present invention provides a method for use in diagnosing the presence, absence or degree of oedema, wherein the apparatus includes:
a) at least two electrode systems, each electrode system including:
   i) a signal generator for applying a first signal to be applied to the subject;
   ii) a sensor for sensing a second signal across the subject;
   iii) a first electrode for coupling the signal generator to the subject; and,
   iv) a second electrode for coupling the sensor to the subject; and,
b) a measuring device for controlling the electrode systems to allow impedance measurements to be performed; and,
c) at least two leads for connecting the measuring device to the electrode systems, and wherein the method includes, arranging the leads to at least one of:
   i) extend from the measuring device in different directions to thereby reduce inductive coupling therebetween; and,
   ii) minimise the lead length.

In a twelfth broad form the present invention provides a method for use in diagnosing the presence, absence or degree of oedema, wherein the method includes:
a) causing at least one electrical signal to be applied to the subject via first leads operatively connected to first electrodes provided on the subject;
b) determining a first indication indicative of at least one first electrical signal measured via second leads operatively disconnected from second electrodes positioned on the subject;
c) determining a second indication indicative of at least one second electrical signal measured via second leads operatively connected to second electrodes positioned on the subject; and,
d) determining from the indications and the at least one applied signal, at least one instantaneous impedance value.

In a thirteenth broad form the present invention provides a method for use in diagnosing the presence, absence or degree of oedema, wherein the method includes:
a) causing at least one electrical signal to be applied to the subject via first leads operatively connected to first electrodes provided on the subject;
b) determining a first indication indicative of at least one first electrical signal measured via second leads operatively disconnected from second electrodes positioned on the subject;
c) determining a second indication indicative of at least one second electrical signal measured via second leads operatively connected to second electrodes positioned on the subject; and,
d) determining from the indications and the at least one applied signal, at least one instantaneous impedance value.

In a fourteenth broad form the present invention provides apparatus for use in diagnosing the presence, absence or degree of oedema, wherein the apparatus includes a processing system for:
  a) causing at least one electrical signal to be applied to the subject via first leads operatively connected to first electrodes provided on the subject;
  b) determining a first indication indicative of at least one first electrical signal measured via second leads operatively disconnected from second electrodes positioned on the subject;
  c) determining a second indication indicative of at least one second electrical signal measured via second leads operatively connected to second electrodes positioned on the subject; and,
  d) determining from the indications and the at least one applied signal, at least one instantaneous impedance value.

In a fifteenth broad form the present invention provides a method for use in determining body composition, wherein the method includes:
  a) causing at least one electrical signal to be applied to the subject via first leads operatively connected to first electrodes provided on the subject;
  b) determining a first indication indicative of at least one first electrical signal measured via second leads operatively disconnected from second electrodes positioned on the subject;
  c) determining a second indication indicative of at least one second electrical signal measured via second leads operatively connected to second electrodes positioned on the subject; and,
  d) determining from the indications and the at least one applied signal, at least one instantaneous impedance value.

In a sixteenth broad form the present invention provides apparatus for use in determining body composition, wherein the apparatus includes a processing system for:
  a) causing at least one electrical signal to be applied to the subject via first leads operatively connected to first electrodes provided on the subject;
  b) determining a first indication indicative of at least one first electrical signal measured via second leads operatively disconnected from second electrodes positioned on the subject;
  c) determining a second indication indicative of at least one second electrical signal measured via second leads operatively connected to second electrodes positioned on the subject; and,
  d) determining from the indications and the at least one applied signal, at least one instantaneous impedance value.

It will be appreciated that the broad forms of the invention may be used individual or in combination, and may be used for diagnosis of the presence, absence or degree of a range of conditions and illnesses, including, but not limited to oedema, pulmonary oedema, lymphodema, body composition, cardiac function, and the like.

BRIEF DESCRIPTION OF THE DRAWINGS

An example of the present invention will now be described with reference to the accompanying drawings, in which.

DETAILED DESCRIPTION OF THE PREFERRED EMBODIMENTS

Figure 1:
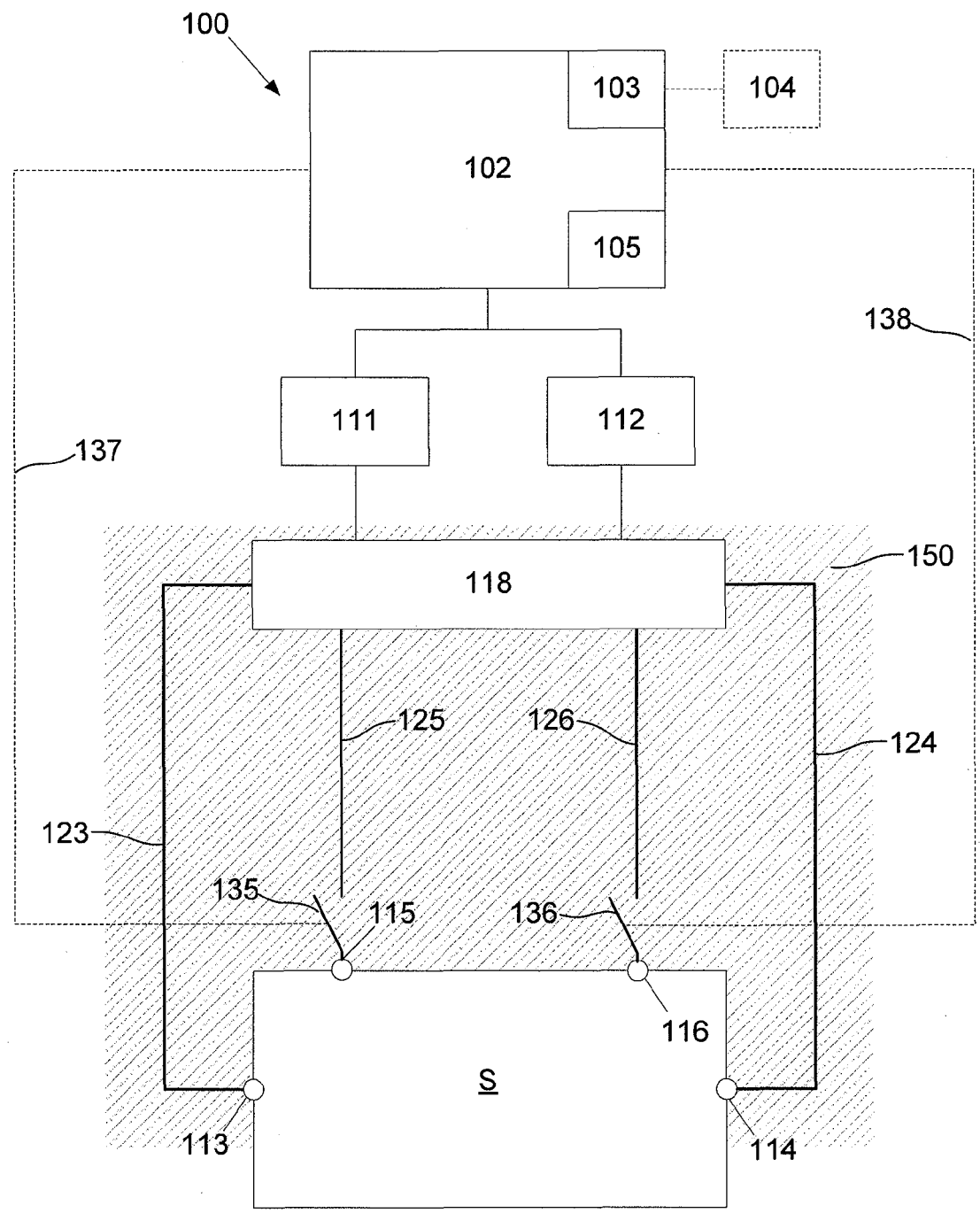
FIG. 1 is a schematic diagram of an example of impedance measuring apparatus.

An example of apparatus suitable for performing an analysis of a subject's bioelectric impedance will now be described with reference to FIG. 1.

As shown the apparatus includes a measuring device 100 including a processing system 102 coupled to a signal generator 111 and a sensor 112. In use the signal generator 111 and the sensor 112 are coupled to first electrodes 113, 114, and second electrodes 115, 116, provided on a subject S, via respective first leads 123, 124, and second leads 125, 126. The connection may be via a switching device 118, such as a multiplexer, allowing the leads 123, 124, 125, 126 to be selectively interconnected to signal generator 111 and the sensor 112.

In this example, the second leads 125, 126 are connected to the second electrodes 115, 116, via respective switches 135, 136. In use, the switches 135, 136 can be controlled by the processing system 102 using suitable wired or wireless control connections, shown generally by dotted lines at 137, 138.

An optional external interface 103 can be used to couple the measuring device 100 to one or more peripheral devices 104, such as an external database or computer system, barcode scanner, or the like. The processing system 102 will also typically include an I/O device 105, which may be of any suitable form such as a touch screen, a keypad and display, or the like.

In use, the processing system 102 is adapted to generate control signals, which causes the signal generator 111 to generate one or more alternating signals, such as voltage or current signals, which can be applied to a subject S, via the first electrodes 113, 114. The sensor 112 then determines the voltage across or current through the subject S, using the second electrodes 115, 116 and transfers appropriate signals to the processing system 102.

Accordingly, it will be appreciated that the processing system 102 may be any form of processing system which is suitable for generating appropriate control signals and interpreting an indication of the measured signals to thereby determine the subject's bioelectrical impedance, and optionally determine other information such as cardiac parameters, the presence absence or degree of oedema, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like.

It will be appreciated that the processing system 102, the signal generator 111 and the sensor 112 may be integrated into a common housing and therefore form an integrated device. Alternatively, the processing system 102 may be connected to the signal generator 111 and the sensor 112 via wired or wireless connections. This allows the processing system 102 to be provided remotely to the signal generator 111 and the sensor 112. Thus, the signal generator 111 and the sensor 112 may be provided in a unit near, or worn by the subject S, whilst the processing system 102 is situated remotely to the subject S.

In one example, the first electrodes 113, 114 are placed on the thoracic and neck region of the subject S. However, this depends on the nature of the analysis being performed. Thus, for example, whilst this electrode arrangement is suitable for cardiac function analysis, in lymphoedema, the electrodes would typically be positioned on the limbs, as required.

Once the electrodes are positioned, one or more alternating signals are applied to the subject S, via the first leads 123, 124 and the first electrodes 113, 114. The nature of the alternating signal will vary depending on the nature of the measuring device and the subsequent analysis being performed.

For example, the system can use Bioimpedance Analysis (BIA) in which a single low frequency signal is injected into the subject S, with the measured impedance being used as required. In contrast Bioimpedance Spectroscopy (BIS) devices perform impedance measurements at multiple frequencies over a selected frequency range. Whilst any range of frequencies may be used, typically frequencies range from very low frequencies (4 kHz) to higher frequencies (15000 kHz). Similarly, whilst any number of measurements may be made, in one example the system can use 256 or more different frequencies within this range, to allow multiple impedance measurements to be made within this range.

Thus, the measuring device 100 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is a frequency rich current from a current source clamped, or otherwise limited, so it does not exceed the maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

Application of the signal typically results in the creation of a varying magnetic field in the region surrounding the leads first 123, 124. However, as shown generally in FIG. 1, the required electrode geometry, and in particular the need to position the second electrodes 115, 116 inwardly of the first electrodes 113, 114 results in the formation of a loop defined by the first leads 123, 124, the subject S and the measuring device 100. This results in a magnetic field being generated as shown generally at 150, with the second leads 125, 126 provided within the magnetic field.

A potential difference and/or current are measured between the second electrodes 115, 116. The acquired signal and the measured signal will be a superposition of potentials generated by the human body, such as the ECG (electrocardiogram), potentials generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as correlating the signal. This can be achieved by multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce an amplitude and phase signal at each frequency.

As part of the above described process, the distance between the second electrodes may be measured and recorded. Similarly, other parameters relating to the subject may be recorded, such as the height, weight, age, sex, health status, any interventions and the date and time on which they occurred. Other information, such as current medication, may also be recorded. This can then be used in performing further analysis of the impedance measurements, so as to allow determination of the presence, absence or degree of oedema, to assess body composition, or the like.

To assist accurate measurement of the impedance, buffer circuits may be placed in connectors that are used to connect the second electrodes 115, 116 to the second leads 125, 126, as will be described in more detail below. This ensures accurate sensing of the voltage response of the subject S, and in particular helps eliminate contributions to the measured voltage due to the response of the second leads 125, 126, and reduce signal loss.

This in turn greatly reduces artefacts caused by movement of the second leads 125, 126, which is particularly important in applications such as monitoring fluid levels during dialysis, in which sessions usually last for several hours and the subject will move around and change positions during this time.

A further option is for the voltage to be measured differentially, meaning that the sensor used to measure the potential at each second electrode 115, 116 only needs to measure half of the potential as compared to a single ended system.

The measurement system may also have buffers placed in the connectors between the first electrodes 113, 114 and the first leads 123, 124. In one example, current can also be driven or sourced through the subject S differentially, which again greatly reduced the parasitic capacitances by halving the common-mode current. Another particular advantage of using a differential system is that the micro-electronics built into the connectors for each first electrode 113, 114 also removes parasitic capacitances that arise when the subject S, and hence the leads first 123, 124, move.

Figure 2:
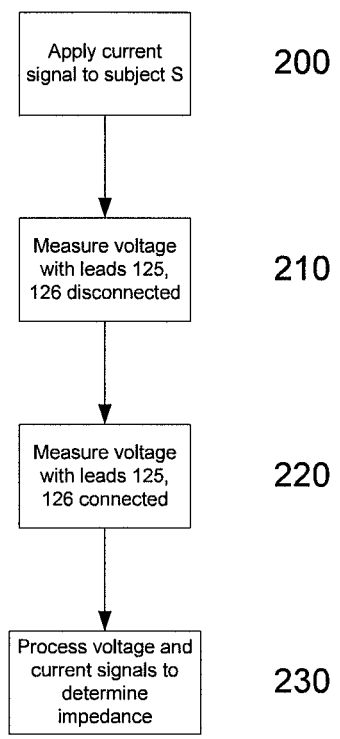
FIG. 2 is a flowchart of an example of a process for performing impedance measurements using the apparatus of FIG. 1.

An example of the operation of the apparatus for performing impedance analysis will now be described with reference to FIG. 2.

At step 200, a signal is applied to the subject S, via the first leads 123, 124 and the first electrodes 113, 114. At step 210, a first indication indicative of the signal induced within the second leads 125, 126 is determined. Typically this is achieved by having the sensor 112 sense a first signal whilst the second leads 125, 126 are operatively disconnected from the second electrodes 115, 116, with the first indication being a digitised version of the sensed first signal.

At step 220, a second indication indicative of the signal induced within the subject S is determined. Again, this is typically achieved having the sensor 112 sense a second signal from the second leads 125, 126 whilst the second leads 125, 126 are operatively connected to the secondly electrodes 115, 116 with the second indication being a digitised version of the sensed second signal.

It will be appreciated that steps 210 and 220 may be performed in any order, and that the above order is for the purpose of example only.

The operative disconnection may be achieved through physical separation of each second lead 125, 126 and the corresponding second electrode 115, 116. Thus, for example, an operator may detach the second lead 125, 126 from the corresponding second electrode 115, 116, and then reattach the second leads 125, 126 and the second electrodes 115, 116 when the subject's impedance is to be measured.

However, it is preferable that the second leads 125, 126 are provided in the same physical geometry as is used for the measurement at step 220, and accordingly, the operative disconnection may be achieved using the switches 135, 136. In this example, the switches 135, 136 are provided in an open position at step 210, and a closed position at step 220.

It will also be appreciated that a range of alternative mechanisms for operative disconnection may be used. Thus, for example, instead of using switches 135, 136 that physically disconnect the leads and the electrodes, operative disconnection may be achieved by effective disconnection. This could be achieved by using resistors in place of the switches 135, 136, to alter the impedance of the connection between the second leads 125, 126 and the second electrodes 115, 116. In this instance, by using variable resistors, the resistance or impedance can be increased when it is desired to operatively disconnect the second leads 125, 126 and the second electrodes 115, 116. Similarly, the resistance/impedance can be decreased when it is desired to operatively connect the second leads 125, 126 and the second electrodes 115, 116. It will be appreciated that other similar techniques could also be used.

At step 230 the measuring device 100 operates to analyse the current and voltage signals to allow impedance values indicative of the subject's impedance to be determined. In one example, this is achieved by using the first and second indications, for example by subtracting the first voltage from the second voltage. Alternatively any suitable modification of the second voltage using the first voltage can be performed. A further alternative is to calculate first and second impedance values from the first and second voltages and then modify the second impedance values using the first impedance values.

It will be appreciated that the magnitude of the inductive coupling effect will depend on the frequency of the applied current, and accordingly, if measurements are to be performed at multiple frequencies, then typically steps 210 and 220 would be performed at each frequency.

In the event that a superposition is used, then steps 210 and 220 would be repeated for each superposition of frequencies. Thus, a signal formed from a superposition of frequencies would be applied at step 210, with the second leads 125, 126 and the second electrodes 115, 116 operatively disconnected. The same signal would then be reapplied at step 220, with the second leads 125, 126 and the second electrodes 115, 116 operatively connected.

Figure 3:
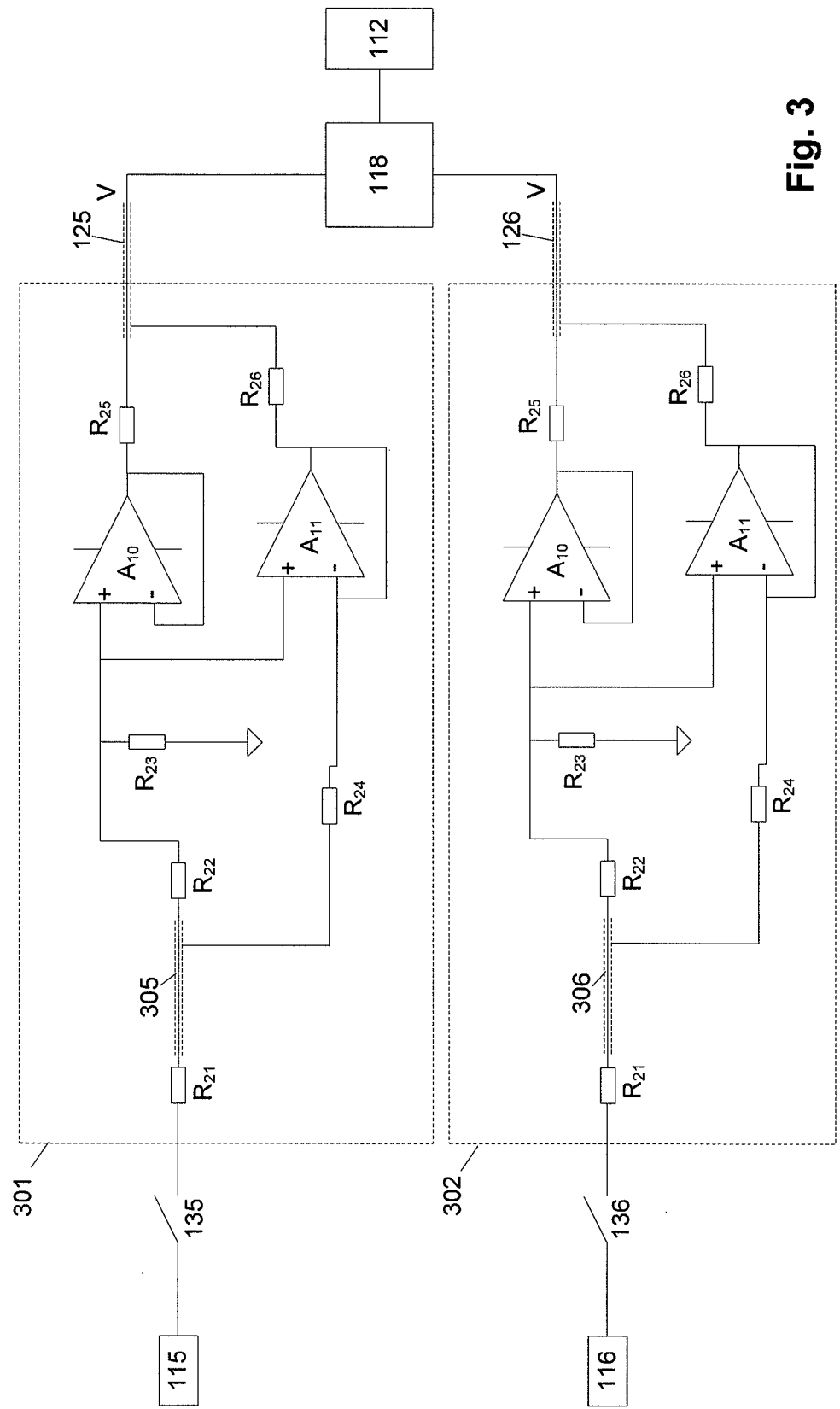
FIG. 3 is a schematic diagram of an example of a buffer circuit for use in the apparatus of FIG. 1.

An example of voltage buffer circuit is shown in FIG. 3. In this example, each second electrode 115, 116, is coupled to a respective buffer circuit 301, 302.

In this example, each buffer 301, 302 includes amplifiers $A_{10}$, $A_{111}$, and a number of resistors $R_{21}$, ..., $R_{26}$, interconnected as shown. In use, each buffer 301, 302, is connected a respective electrode 115, 116 via connections 305, 306. The buffers 301, 302 are also connected via leads 125, 126 to the switching unit 118 and the sensor 112, which in one example is formed from a differential amplifier. It will therefore be appreciated that a respective buffer circuit 301, 302 is connected to each of the electrodes 115, 116, and then to the differential amplifier 112, allowing the potential difference across the subject S to be determined.

In use, each amplifier $A_{10}$ amplifies the detected signals and drives the core of the respective cables forming the second leads 125, 126 whilst each amplifier $A_{11}$ amplifies the detected signal and drives the respective shield of the cables forming the second leads 125, 126. Resistors $R_{26}$ and $R_{25}$ decouple the amplifier outputs from the capacitances associated with cable, although the need for these depends on the amplifier selected. This allows multi-core shielded cables to be used to establish the connections to the second electrodes 115, 116.

As shown, the buffer circuits 301, 302 are connected to the second electrodes 115, 116, via the switches 135, 136. By positioning the switches 135, 136 between the second electrodes 125, 126 and the buffer circuits 301, 302, this ensures any voltages induced within the buffer circuit, due to the inductive coupling effect, are also taken into account.

Figure 4A:
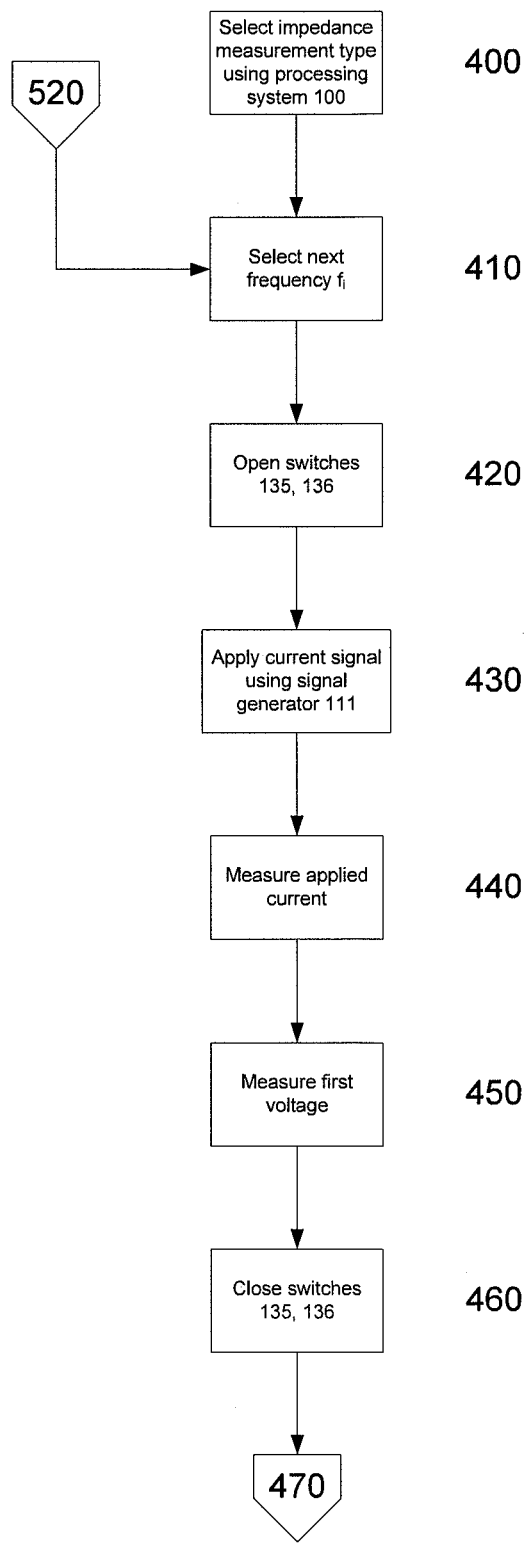
FIGS. 4A and 4B are a flowchart of a second example of a process for performing impedance measurements using the apparatus of FIG. 1.
Figure 4B:
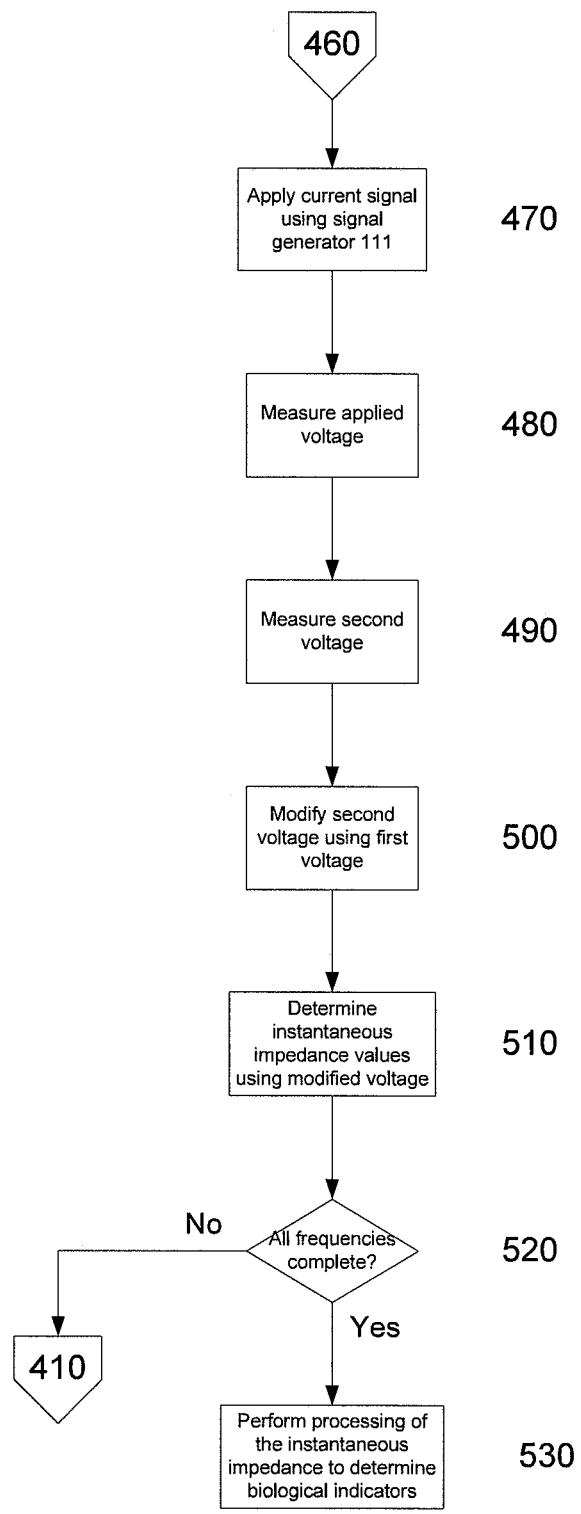

A second example operation of the apparatus will now be described with reference to FIGS. 4A to 4C.

At step 400 an operator selects an impedance measurement type using the processing system 100. This may be achieved in a number of ways and is typically achieved by having the processing system 100 display a user interface including a list of available measurement procedures, allowing a desired procedure to be selected using the I/O device 142. Additionally, or alternatively, the operator can define custom procedures.

Available procedures are typically stored as profiles in the memory 141, and describe the sequence of measurements that are to be performed. This includes information regarding the signals that need to be generated by the signal generator 111, and the relative timing with which the signals should be applied to the subject S. The profiles also include an indication of calculations that need to be performed on recorded measurements, to allow body composition or other biological or health status indicators to be determined.

Thus, for example, when performing cardiac function determination, it will be typical to use a different applied current sequence and a different impedance analysis, as compared to performing lymphoedema measurements, body composition, pulmonary oedema detection, or the like.

Once an appropriate measurement type has been selected by the operator, this will cause the processing system 100 to select a next frequency $f_i$ for the current signal to be applied, at step 410.

At step 420, the processing system 100 causes the switches 135, 136 to be opened. This can be achieved in any suitable manner, and may depend to a large extent on the nature of the switches. For example, if the switches are manually operated, this may require that the processing system 100 display an indication that the switches should be opened, with the operator providing confirmation of this once the switches are opened. However, preferably the switches are electronically controlled by the processing system 100, allowing the process to be performed automatically. This may be achieved in any suitable manner.

At step 430, the processing system 100 causes the signal generator 111 to generate an alternating current at the frequency $f_i$, with this being applied to the subject S via the leads 123, 124 and the electrodes 123, 124, with an indication of the applied current optionally being returned to the processing system 100 at step 440. This may not be required if the applied current is determined solely based on control of the signal generator by the processing system 100, or if it is alternatively measured at step 480 below.

Simultaneously, at step 450, the first voltage induced in the leads 125, 126 is measured using the sensor 112, with a first indication indicative of the measured voltage being returned to the processing system 100.

At step 460, the processing system 100 causes the switches 135, 136 to close, before causing the signal generator 111 to apply an alternating current at the frequency $f_i$, to the subject S, at step 470. An indication of the applied signal is optionally returned to the processing system 1000 at step 480. Simultaneously, at step 490, the second voltage induced in the subject S and the second leads 125, 126 is measured using the sensor 112, with a second indication indicative of the measured voltage being returned to the processing system 100.

It will be appreciated that either step 440 or step 480 may not be required if the signal generator is sufficiently stable to supply a consistent current at steps 430 and 470, or if an impedance of the leads induced by the inductive coupling is not used in the analysis.

In this example, at step 500 the second voltage is modified using the first voltage, either by subtracting the first voltage from the second voltage, by scaling the second voltage, or the like. The modified second voltage and the applied current are then used to determine instantaneous impedance values, at step 510.

As an alternative, at step 500 first and second impedance values can be determined based on the first and second voltages respectively, with the first impedance values being used to modify the second impedance values.

During the processing of the current and voltage signals additional processing may also be performed depending on the impedance measurement profile, such as processing the voltage signals V to extract ECG signals. The signals will also typically be filtered to ensure that only signals at the applied frequencies $f_i$, are used in impedance determination. This helps reduce the effects of noise, as well as reducing the amount of processing required.

At step 520, it is determined if all frequencies required by the profile have been completed, and if not the process returns to step 410 to allow the next frequency to be used. Otherwise, at step 530 the impedance values are analysed to allow biological indicators to be determined, as will be appreciated by persons skilled in the art.

In the above described process, the first and second voltages are determined at each measurement frequency in turn. As an alternative, the process may involve determining the first voltage at each frequency and then subsequently determining the second voltage at each frequency, or vice versa. However, by performing the first and second voltage measurement at each frequency in turn, this helps ensure that the first and second leads 123, 124, 125, 126, are in similar positions when the first and second voltages are measured, helping to ensure the inductive coupling effect is the same in both cases. In contrast, if the first voltage measurements are performed first, then by the time the second voltage measurements are performed, the subject S and hence the leads 123, 124, 125, 126 may have moved, thereby altering the effect of the inductive coupling and hence reducing the effectiveness of the above described process.

An example of an alternative apparatus will now be described with reference to FIG. 5. In this example, components similar to those shown in FIG. 1 use similar reference numerals.

In this example, the second leads 125, 126 are formed from lead pairs 525A, 525B and 526A, 526B, each of which includes a respective buffer circuit 545A, 546A, 545B, 546B, similar to the buffers 301, 302. In this example, the leads 525A, 526A are connected to the electrodes 115, 116 allowing the second voltages to be measured, whilst the leads 525B, 526B remain unconnected allowing the first voltages to be measured.

Accordingly, it will be appreciated that this arrangement allows the first and second voltages to be measured simultaneously, which in turn helps ensure all the leads 123, 124, 525A, 526A, 525B, 526B are in the same positions when the measurements are made, ensuring all each second lead pair 525A, 525B; 526A, 526B is subject to the same inductive coupling effect. Furthermore, performing the measurements simultaneously reduces the length of time the measurement process takes and avoids the need for the switches 135, 136.

To assist with accurate cancellation of the inductive coupling effect, it is typical to ensure that each lead in a lead pair 525A, 525B; 526A, 526, has a similar responsiveness to the inductive coupling effect. This can be achieved by ensuring the impedance of each of the leads in a lead pair 525A, 525B; 526A, 526 and the associated buffer circuits 545A, 545B; 546A, 546B are matched as closely as possible. As this can increase the complexity and cost of manufacture, in some examples it may be preferred to use the apparatus of FIG. 1 whilst in other situations, the apparatus of FIG. 5 may be more suitable.

In any event, by independently measuring voltages induced in the leads separately to measuring the voltage induced in the subject, the above described process allows for inductive coupling between signal supply and signal measurement leads to be accounted for. This helps improve the accuracy of the measurement process and hence the accuracy of any determined impedance values or biological indicators.

A further example of apparatus for analysis of a subject's bioelectric impedance will now be described with reference to FIG. 6.

As shown the apparatus includes a measuring device 600 including a processing system 602, connected to one or more signal generators 617A, 617B, via respective first leads 623A, 623B, and to one or more sensors 618A, 618B, via respective second leads 625A, 625B. As in the example of FIG. 1, the connection may be via a switching device, such as a multiplexer, although this is not essential.

In use, the signal generators 617A, 617B are coupled to two first electrodes 613A, 613B, which therefore act as drive electrodes to allow signals to be applied to the subject S, whilst the one or more sensors 618A, 618B are coupled to the second electrodes 66A, 66B, which therefore act as sense electrodes.

The signal generators 617A, 617B and the sensors 618A, 618B may be provided at any position between the processing system 602 and the electrodes 613A, 613B, 66A, 66B, and may therefore be integrated into the measuring device 600. However, in one example, the signal generators 617A, 617B and the sensors 618A, 618B are integrated into an electrode system, or another unit provided near the subject S, with the leads 623A, 623B, 625A, 625B connecting the signal generators 617A, 617B and the sensors 618A, 618B to the processing system 602.

It will be appreciated that the above described system is a two channel device, with each channel being designated by the suffixes A, B respectively. The use of a two channel device is for the purpose of example only, as will be described in more detail below.

An optional external interface 602 can be used to couple the measuring device 600, via wired, wireless or network connections, to one or more peripheral devices 604, such as an external database or computer system, barcode scanner, or the like. The processing system 602 will also typically include an I/O device 605, which may be of any suitable form such as a touch screen, a keypad and display, or the like.

In use, the processing system 602 functions in a similar manner to the processing system 102 of FIG. 1, and is therefore adapted to generate control signals, which cause the signal generators 617A, 617B to generate one or more alternating signals, such as voltage or current signals of an appropriate waveform, which can be applied to a subject S, via the first electrodes 613A, 613B. The sensors 618A, 618B then determine the voltage across or current through the subject S, using the second electrodes 615A, 615B and transfer appropriate signals to the processing system 602.

Accordingly, it will be appreciated that the processing system 602 may be any form of processing system which is suitable for generating appropriate control signals and at least partially interpreting the measured signals to thereby determine the subject's bioelectrical impedance, and optionally determine other information such as the presence, absence or degree of oedema, or the like.

The processing system 602 may therefore be a suitably programmed computer system, such as a laptop, desktop, PDA, smart phone or the like. Alternatively the processing system 602 may be formed from specialised hardware, such as an FPGA (field programmable gate array), or a combination of a programmed computer system and specialised hardware, or the like, as will be described in more detail below.

In use, the first electrodes 613A, 613B are positioned on the subject to allow one or more signals to be injected into the subject S. The location of the first electrodes will depend on the segment of the subject S under study. Thus, for example, the first electrodes 613A, 613B can be placed on the thoracic and neck region of the subject S to allow the impedance of the chest cavity to be determined for use in cardiac function analysis. Alternatively, positioning electrodes on the wrist and ankles of a subject allows the impedance of limbs and/or the entire body to be determined, for use in oedema analysis, or the like.

Once the electrodes are positioned, one or more alternating signals are applied to the subject S, via the first leads 623A, 623B and the first electrodes 613A, 613B, in a manner similar to that described above. 6

Thus, the measuring device 600 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically and/or differentially arranged, with each of the signal generators 617A, 617B being independently controllable, to allow the potential across the subject to be varied.

A potential difference and/or current is measured between the second electrodes 66A, 66B. In one example, the voltage is measured differentially, meaning that each sensor 618A, 618B is used to measure the potential at each second electrode 66A, 66B and therefore need only measure half of the potential as compared to a single ended system.

The measured signal can then be analysed as described above to allow impedance measurements to be determined.

The accuracy of the measurement of impedance can be subject to a number of other external factors, in addition to the inductive coupling described above. These can include, for example, the effect of capacitive coupling between the subject and the surrounding environment, as well as between the leads and the subject, which will vary based on factors such as lead construction, lead configuration, subject position, or the like. Additionally, there are typically variations in the impedance of the electrical connection between the electrode surface and the skin (known as the "electrode impedance"), which can depend on factors such as skin moisture levels, melatonin levels, or the like. It can also be caused by different electrode sizes and pressure on the electrodes. A further source of error is the presence of inductive coupling between different electrical connections within the leads, or between the leads themselves.

Such external factors can lead to inaccuracies in the measurement process and subsequent analysis and accordingly, it is desirable to be able to reduce the impact of external factors on the measurement process.

As certain external factors, such as parasitic capacitances and inductive coupling, will affect the signals within each of the leads, it is preferable to perform the impedance measurements in such a way that the applied signal results in a symmetrical voltage about the sensing electrodes. The reason for this is that if the voltages sensed at the electrodes are unsymmetrical (a situation referred to as an "imbalance"), then differences in the magnitude of signals within the leads can lead to differing effects due to noise and interference.

For example, an imbalance will result in smaller voltage signals in one of the sets of leads, which can be more adversely effected by noise and other external effects. Thus, if this voltage is sufficiently small, it can be swamped by voltages arising due to inductive effects, or the like. Additionally, larger voltages in one of the leads can lead to larger parasitic capacitances and inductive coupling associated with that respective lead. These effects can therefore lead to a reduced accuracy for any resulting calculated impedance.

An imbalance can arise due to a number of different reasons, for example if there are different contact impedances between the electrodes and the subject, as well as if there are different contact areas, contact pressures, or the like, and it will be appreciated that issues such as this can be difficult avoid.

The presence of an imbalance, where the potential across the subject is not symmetrical with respect to the effective centre of the subject, leads to a "common mode" signal, which is effectively a measure of the signal at the subject that is unrelated to the subject's impedance.

To help reduce this effect, it is therefore desirable for signals to be applied to the subject so that they result in a symmetrical voltage about the sensing electrodes. This typically means that the reference voltage of the measurement apparatus will be close to the effective centre point of the subject, as considered relative to the electrode placement.

In one example, a symmetrical voltage about the sensing electrodes can be achieved by using a symmetrical voltage source, such as a differential bidirectional voltage drive scheme, which applies a symmetrical voltage to each of the drive electrodes 613A, 613B. However, this is not always effective if the electrode impedances for the two drive electrodes 613A, 613B are unmatched, which is typical in a practical environment.

In one example, the apparatus overcomes this by adjusting the differential drive voltages applied to each of the drive electrodes 613A, 613B, to compensate for the different electrode impedances, and thereby restore the desired symmetry of the voltage at the sense electrodes 615A, 615B. This process is referred to herein as balancing and in one example, helps reduce the magnitude of the common mode signal, and hence reduce current losses caused by parasitic capacitances associated with the subject.

The degree of imbalance, and hence the amount of balancing required, can be determined by monitoring the signals at the sense electrodes 615A, 615B, and then using these signals to control the signal applied to the subject via the drive electrodes 613A, 613B. In particular, the degree of imbalance can be calculated using the voltages detected at the sense electrodes 615A, 615B.

In one example, the voltages sensed at each of the sense electrodes 615A, 615B are used to calculate a first voltage, which is achieved by combining or adding the measured voltages. Thus, the first voltage can be an additive voltage (commonly referred to as a common mode voltage or signal) which can be determined using a differential amplifier.

In this regard, a differential amplifier is typically used to combine two sensed voltage signals $V_a$, $V_b$, to determine a second voltage, which in one example is a voltage differential $V_a-V_b$ across the points of interest on the subject, which is used in conjunction with a measurement of the current flow through the subject to derive impedance values. However, some differential amplifiers provide a "common mode" signal $(V_a+V_b)/2$, which is a measure of the common mode voltage.

Whilst some differential amplifiers include a common mode rejection capability, this is generally of only finite effect and typically reduces in effectiveness at higher frequencies, so a large common mode signal will produce an error signal superimposed on the differential signal.

By determining the magnitude of the common mode signal, the applied voltages can then be adjusted, for example by adjusting the relative magnitude and/or phase of the applied signal, to thereby minimise the common mode signal and substantially eliminate any imbalance.

An example of the operation of the apparatus of FIG. 6 to perform this will now be described with reference to FIG. 7.

At step 700, a signal is applied to the subject S, via the first electrodes 613A, 613B, with the voltage signals measured across the subject S being determined at step 710. This will typically be achieved using the techniques outlined above.

At step 720, any imbalance is determined by the processing system 602 using the first voltage derived from the potentials measured at each of the second electrodes 615A, 615B, which in one example represents a common mode signal At step 730, the measuring device 600 optionally adjusts the signal applied to the subject S, so as to reduce the imbalance and hence the magnitude of any common mode signal. Thus, the signal applied at either one of the first electrodes 613A, 613B can be adjusted, for example by increasing or decreasing the relative signal magnitudes and/or altering the relative signal phases, so as to balance the signal within the subject and centralise the position of the reference potential within the subject, relative to the electrode positioning.

At step 740, the measuring device can then determine the signal applied to the subject and the potentials measured at the electrodes 613A, 613B, thereby allowing an impedance to be determined at step 750.

As the position of the reference is impedance dependent, then the position of the reference potential within the subject, and hence the imbalance will typically vary depending on the frequency of the applied signal. Accordingly, in one example, it is typical to determine the imbalance and adjust the applied signal at each applied frequency. However, this may depend on the particular implementation.

A specific example of the apparatus will now be described in more detail with respect to FIG. 8.

In this example, the measuring system 800 includes a computer system 810 and a separate measuring device 820. The measuring device 820 includes a processing system 830 coupled to an interface 821 for allowing wired or wireless communication with the computer system 810. The processing system 830 may also be optionally coupled to one or more stores, such as different types of memory, as shown at 822, 823, 824, 825, 826.

In one example, the interface is a Bluetooth stack, although any suitable interface may be used. The memories can include a boot memory 822, for storing information required by a boot-up process, and a programmable serial number memory 823, that allows a device serial number to be programmed. The memory may also include a ROM (Read Only Memory) 824, flash memory 825 and EPROM (Electronically Programmable ROM) 826, for use during operation. These may be used for example to store software instructions and to store data during processing, as will be appreciated by persons skilled in the art.

A number of analogue to digital converters (ADCs) 827A, 827B, 828A, 828B and digital to analogue converters (DACs) 829A, 829B are provided for coupling the processing system 830 to the sensors 618A, 618B and the signal generators 617A, 617B, as will be described in more detail below.

A controller, such as a microprocessor, microcontroller or programmable logic device, may also be provided to control activation of the processing system 830, although more typically this is performed by software commands executed by the processing system 830.

Figure 9:
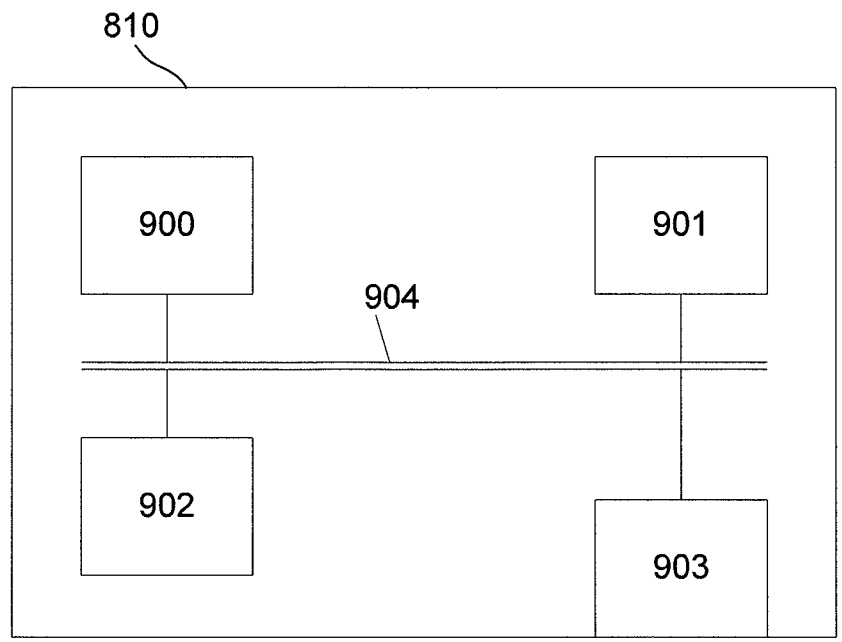
FIG. 9 is a schematic diagram of an example of a computer system.

An example of the computer system 810 is shown in FIG. 9. In this example, the computer system 810 includes a processor 900, a memory 901, an input/output device 902 such as a keyboard and display, and an external interface 903 coupled together via a bus 904, as shown. The external interface 903 can be used to allow the computer system to communicate with the measuring device 820, via wired or wireless connections, as required, and accordingly, this may be in the form of a network interface card, Bluetooth stack, or the like.

In use, the computer system 810 can be used to control the operation of the measuring device 820, although this may alternatively be achieved by a separate interface provided on the measuring device 800. Additionally, the computer system can be used to allow at least part of the analysis of the impedance measurements to be performed.

Accordingly, the computer system 810 may be formed from any suitable processing system, such as a suitably programmed PC, Internet terminal, lap-top, hand-held PC, smart phone, PDA, server, or the like, implementing appropriate applications software to allow required tasks to be performed.

In contrast, the processing system 830 typically performs specific processing tasks, to thereby reduce processing requirements on the computer system 810. Thus, the processing system typically executes instructions to allow control signals to be generated for controlling the signal generators 617A, 617B, as well as the processing to determine instantaneous impedance values.

In one example, the processing system 830 is formed from custom hardware, or the like, such as a Field Programmable Gate Array (FPGA), although any suitable processing module, such as a magnetologic module, may be used.

In one example, the processing system 830 includes programmable hardware, the operation of which is controlled using instructions in the form of embedded software instructions. The use of programmable hardware allows different signals to be applied to the subject S, and allows different analysis to be performed by the measuring device 820. Thus, for example, different embedded software would be utilised if the signal is to be used to analyse the impedance at a number of frequencies simultaneously as compared to the use of signals applied at different frequencies sequentially.

The embedded software instructions used can be downloaded from the computer system 810.

Alternatively, the instructions can be stored in memory such as the flash memory 825 allowing the instructions used to be selected using either an input device provided on the measuring device 820, or by using the computer system 810. As a result, the computer system 810 can be used to control the instructions, such as the embedded software, implemented by the processing system 830, which in turn alters the operation of the processing system 830.

Additionally, the computer system 810 can operate to analyse impedance determined by the processing system 830, to allow biological parameters to be determined.

Whilst an alternative arrangement with a single processing system may be used, the division of processing between the computer system 810 and the processing system 830 can provide some benefits.

Firstly, the use of the processing system 830 allows the custom hardware configuration to be adapted through the use of appropriate embedded software. This in turn allows a single measuring device to be used to perform a range of different types of analysis.

Secondly, this vastly reduces the processing requirements on the computer system 810. This in turn allows the computer system 810 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of lymphoedema.

Thirdly, this allows the measuring device 820 to be updated. Thus for example, if an improved analysis algorithm is created, or an improved current sequence determined for a specific impedance measurement type, the measuring device can be updated by downloading new embedded software via flash memory 825 or the external interface 821.

In use, the processing system 830 generates digital control signals, which are converted to analogue voltage drive signals $V_D$ by the DACs 829, and transferred to the signal generators 617. Analogue signals representing the current of the drive signal $I_D$ applied to the subject and the subject voltage $V_S$ measured at the second electrodes 615A, 615B, are received from the signal generators 617 and the sensors 618 and are digitised by the ADCs 827, 828. The digital signals can then be returned to the processing system 830 for preliminary analysis.

In this example, a respective set of ADCs 827, 828, and DACs 829 are used for each of two channels, as designated by the reference numeral suffixes A, B respectively. This allows each of the signal generators 617A, 617B to be controlled independently and for the sensors 618A, 618B to be used to detect signals from the electrodes 615A, 615B respectively. This therefore represents a two channel device, each channel being designated by the reference numerals A, B.

In practice, any number of suitable channels may be used, depending on the preferred implementation. Thus, for example, it may be desirable to use a four channel arrangement, in which four drive and four sense electrodes are provided, with a respective sense electrode and drive electrode pair being coupled to each limb. In this instance, it will be appreciated that an arrangement of eight ADCs 827, 828, and four DACs 829 could be used, so each channel has respective ADCs 827, 828, and DACs 829. Alternatively, other arrangements may be used, such as through the inclusion of a multiplexing system for selectively coupling a two-channel arrangement of ADCs 827, 828, and DACs 829 to a four channel electrode arrangement, as will be appreciated by persons skilled in the art.

Figure 10:
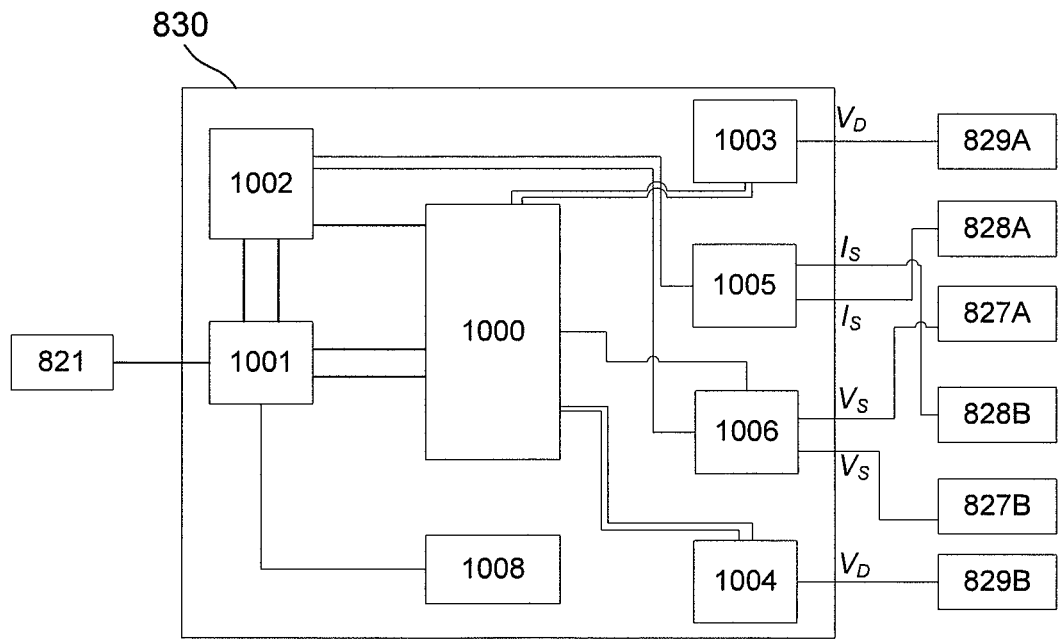
FIG. 10 is a schematic of an example of the functionality of the processing system of FIG. 8.

An example of the functionality implemented by the processing system 830 will now be described with reference to FIG. 10. In this example the processing system 830 implements the functionality using appropriate software control, although any suitable mechanism may be used.

In this example the processing system 830 includes a timing and control module 1000, a messaging module 1001, an analysis module 1002, sine wave look up tables (LUTs) 1003, 1004, a current module 1005, and a voltage module 1006.

In use, the processing system 830 receives information representing the frequency and amplitude of signals to be applied to the subject S from the computer system 810, via the external interface 821. The timing and control module 1000 uses this information to access the LUTs 1003, 1004, which in turn cause a digital sine wave signal to be produced based on the specified frequency and amplitude. The digital voltage signals are transferred to the DAC's 829A, 829B, to thereby allow analogue voltage drive signals $V_D$ to be produced.

Measured analogue voltage and current signals $V_S$, $I_S$ are digitised by the ADC's 827, 828 and provided to the current and voltage modules 1005, 1006. This allows the processing system 830 to determine the current flow by having the current module 1005 determine the total current flow through the subject using the two current signals $I_S$, with an indication of this being provided to the analysis module 1002. The voltage module 1006, which is typically in the form of a differential voltage amplifier, or the like, operates to determine a differential voltage, which is also transferred to the analysis module 1002, allowing the analysis module to determine impedance values using the current and differential voltage signals.

In addition to this, the voltage module 1006 determines a common mode voltage (i.e. a common mode signal), which is returned to the timing and control module 1000. This allows the timing and control module 1000 to determine any imbalance in the voltage sensed at the subject, which as mentioned above is indicative of the device reference potential not being positioned centrally within the subject with respect to the electrodes.

If the degree of imbalance is unacceptable, the timing and control module 1000 can adjust the relative amplitude and/or phase of the sine waves representing the voltage drive signals $V_D$ as will be described below, allowing a new imbalance to be determined.

Once the imbalance is determined to be acceptable the timing and control module 1000 can provide an indication of this to the analysis module 1002, allowing this to use appropriate analysis, such as phase quadrature extraction, to determine a ratio and phase difference for the measured impedance, based on the current flow through the subject and the differential voltage signals. The ratio and phase can then be transferred to the messaging module 1010 allowing an indication of measured impedance to be provided to the computer system 810 via the interface 821.

The processing system 830 may also implement a signal level fault detection module 1008. This monitors the magnitude of signals applied to the subject to determine if these are within acceptable threshold levels. If not, the fault detection module 1008 can cause a message to be transferred to the computer system 810 to allow the process to be halted or to allow an alert to be generated.

Figure 11A:
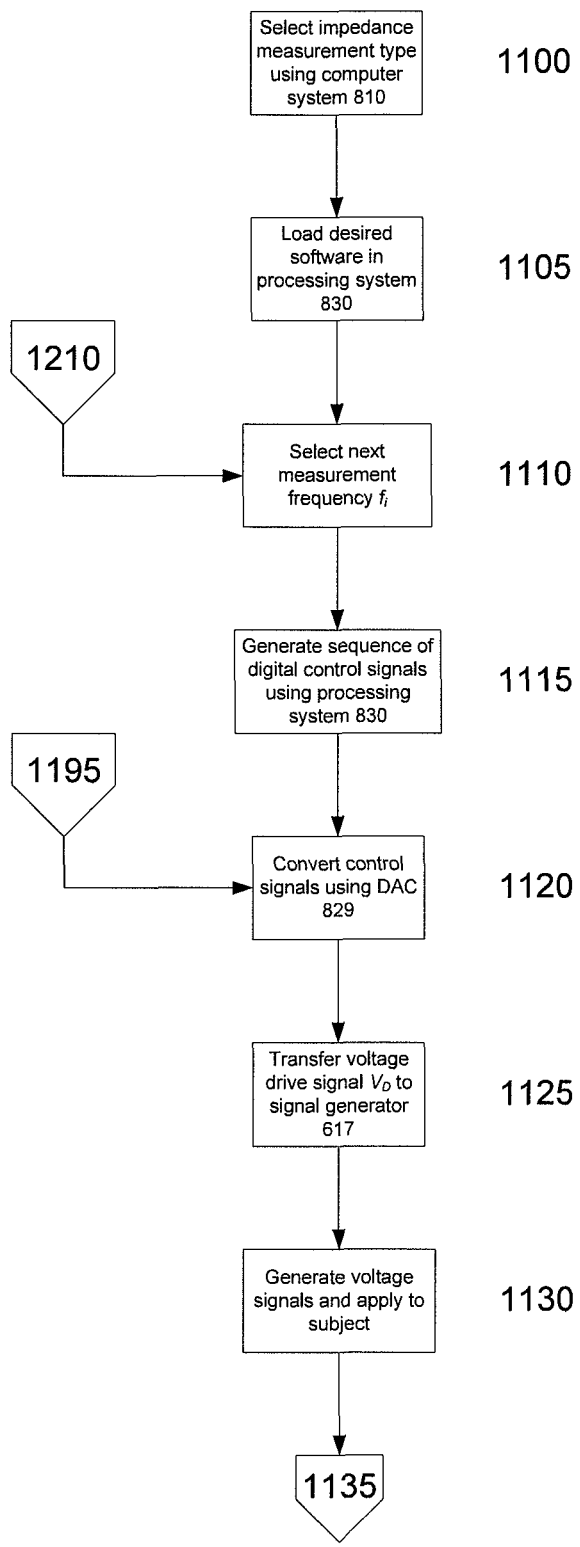
FIGS. 11A to 11C are a flowchart of a second example of a process for performing impedance measurements.
Figure 11B:
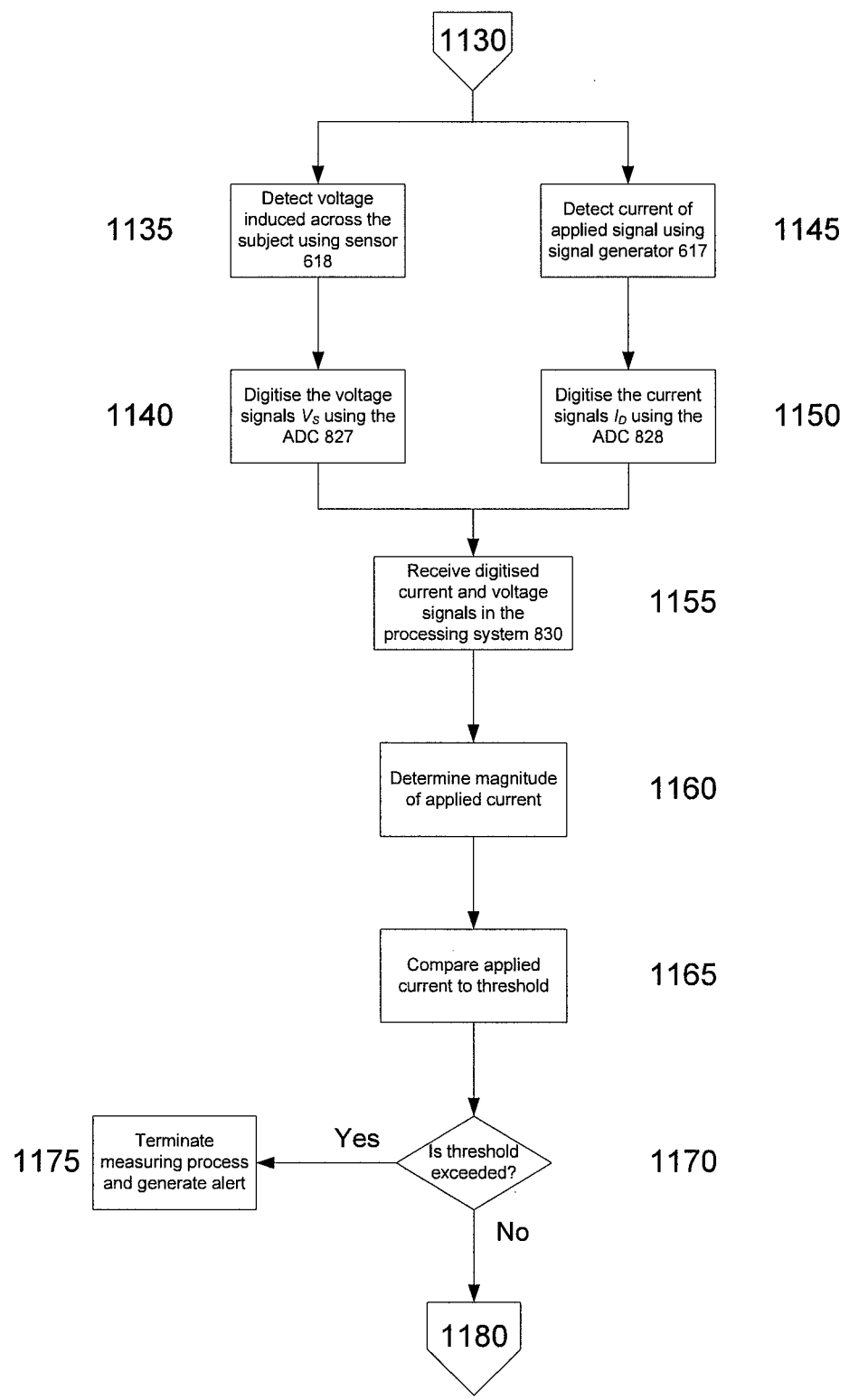
Figure 11C:
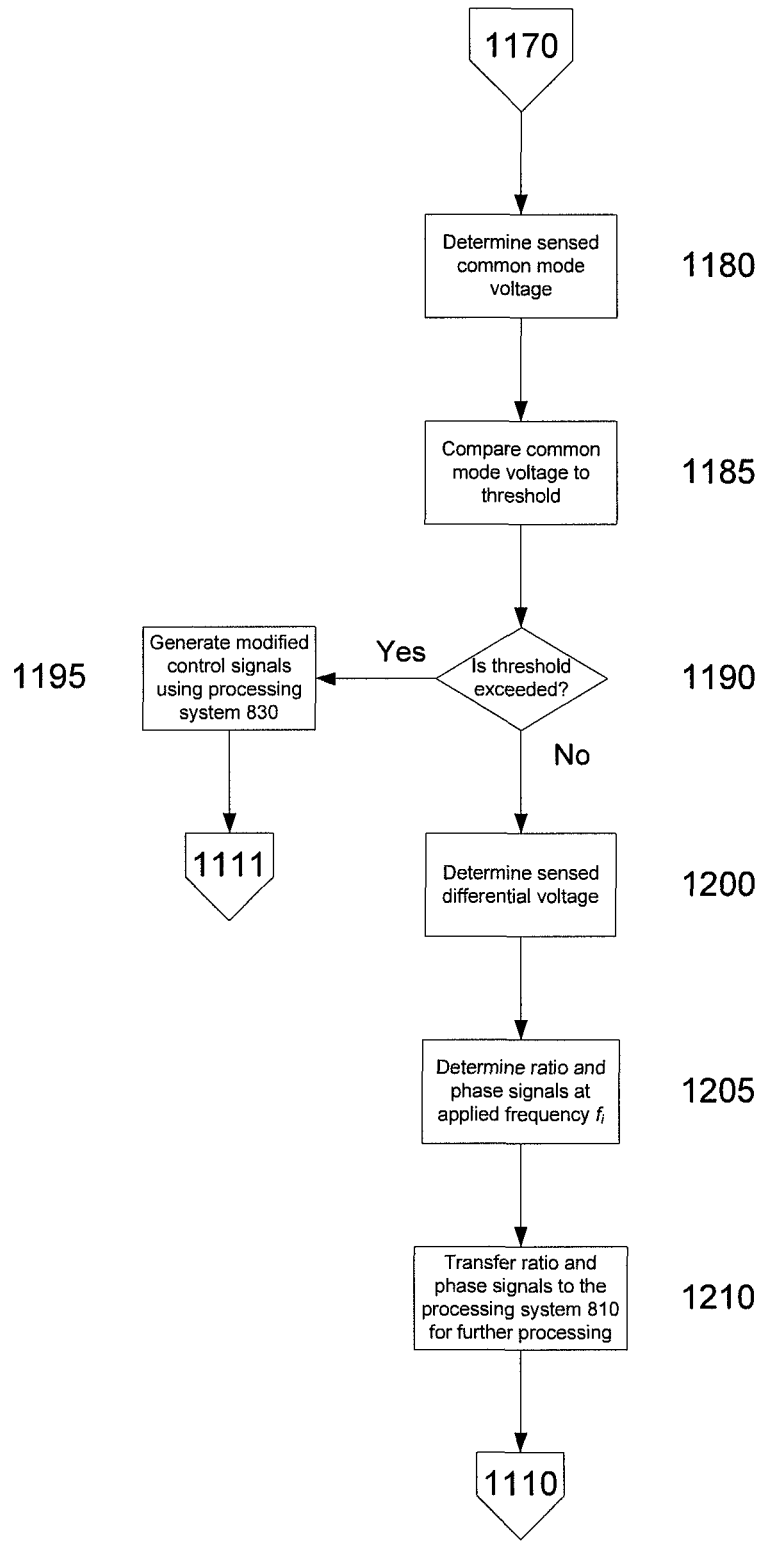

An example of the process for performing impedance measurements will now be described with reference to FIG. 11A to 11C.

At step 1100 the computer system 810 is used to select an impedance measurement type, with this triggering the computer system 810 to cause desired instructions, such as embedded software, to be implemented by the processing system 830. It will be appreciated that this may be achieved in a number of manners, such as by downloading required embedded software from the computer system 810 to the processing system 830 or alternatively by having the processing system 830 retrieve relevant embedded software from internal memory or the like.

At step 1110 the computer system 810 or the processing system 830 selects a next measurement frequency $f_i$, allowing the processing system 830 to generate a sequence of digital voltage control signals at step 1115, as described above. The digital control signals are converted to analogue voltage signals $V_D$ using the DACs 829A, 829B at step 1120, allowing the analogue control signals to be provided to each of the voltage sources 617A, 617B at step 1125. At this point each voltage source 617A, 617B generates respective voltage signals and applies these to the subjects at step 1130, via the respective drive electrodes 613A, 613B.

At step 1135 the voltage induced across the subject is detected via the sense electrodes, 615A, 615B, using the sensors 618A, 618B, with the sensed voltage signals $V_S$ being digitised by the corresponding ADC 827A, 827B at step 1140. At step 1145, simultaneously with this, the current applied to the subject $I_S$, by way of application of the voltage signal, is measured using the signal generators 617A, 617B. An indication of the current injected into the subject $I_S$ is transferred to the ADCs 828A, 828B for digitisation at step 1150.

At step 1155 the digitised current and voltage signals $I_S$, $V_D$ are received by the processing system 830 allowing the processing system 830 to determine the magnitude of the applied current at step 1160. This may be performed using the current module 1005 in the above described functional example of FIG. 10, allowing the fault detection module 1008 to compare the total current flow through the subject to a threshold at step 1165. If it is determined that the threshold has been exceeded at step 1170 then the process may terminate with an alert being generated at step 1175.

This situation may arise, for example, if the device is functioning incorrectly, or there is a problem with connections of electrodes to the subject, such as if one is not in correct electrical contact with the subject's skin. Accordingly, the alert can be used to trigger a device operator to check the electrode connections and/or device operation to allow any problems to be overcome. It will be appreciated, that any suitable form of corrective action may be taken such as attempting to restart the measurement process, reducing the magnitude of the current through the subject, or the like.

At step 1180 the processing system 830 operates to determine a common mode voltage based on the voltage potential sensed at each of the electrodes 615A, 615B, and this is typically achieved using the voltage processing module 1006 in the above functional example. The common mode voltage or common mode signal is then used to determine any imbalance at step 1185.

At step 1190 an assessment is made as to whether the imbalance is acceptable, and it will be appreciated that this may be achieved in any one of a number of ways, such as by comparing the amplitude of the common mode signal to a threshold, or the like. The threshold will generally be previously determined and stored in one of the memories 824, 825, 826, for example during device manufacture or calibration.

In the event that the imbalance is deemed to not be acceptable, then at step 1195 the processing system 830 modifies the digital control signals to reduce the imbalance. This is typically achieved by having the processing system 830 implement an algorithm that adjusts the applied signal to maintain the common mode voltage at the centre of the body as close to the electronics reference or ground potential as possible. This generally involves adjusting the amplitude and/or phase of the voltage signals applied to the subject, using the algorithm. The nature of this adjustment will depend on the nature of the imbalance, as will be appreciated by persons skilled in the art.

The process can then return to step 1120 to allow the modified control signals to be converted to analogue signals using DACs 824, with a modified voltage signal being applied to one or each of the electrodes 613A, 613B. This process is repeated until an acceptable offset is achieved.

Once an acceptable balance is achieved, the processing system 830 operates to determine the differential voltage sensed across the subject at step 1200. In the functional example described above with respect to FIG. 10, this can be achieved using the differential voltage module 1006.

At step 1205 the processing module 830 operates to determine ratio and phase signals, representing the impedance of the subject S, at the applied frequency $f_i$ using the current and differential voltage signals. In the above functional example, this can be performed using the analysis module, and some form of signal analysis, such as phase quadrature analysis, depending on the preferred implementation. At step 1210, an indication of the ratio and phase signals are sent to the computer system 810 for further processing.

Once this is completed the process may return to step 1110 to allow the process to be repeated at a next measurement frequency $f_i$ otherwise if all required frequencies are complete, the measurement process can terminate, allowing the computer system 810 to analyse the impedance measurements, and determine required information, such as any biological indicators, impedance parameters, or the like. The manner in which this is achieved will depend on the type of analysis being performed.

Accordingly, it will be appreciated that by repeating the above described process this allows a number of impedance measurements to be performed over a range of different frequencies. Furthermore, prior to at least one, and more typically, to each measurement, a check can be performed to ensure that the common mode of the subject and the device are approximately matched, thereby reducing inaccuracies in the measurement procedure.

Figure 12:
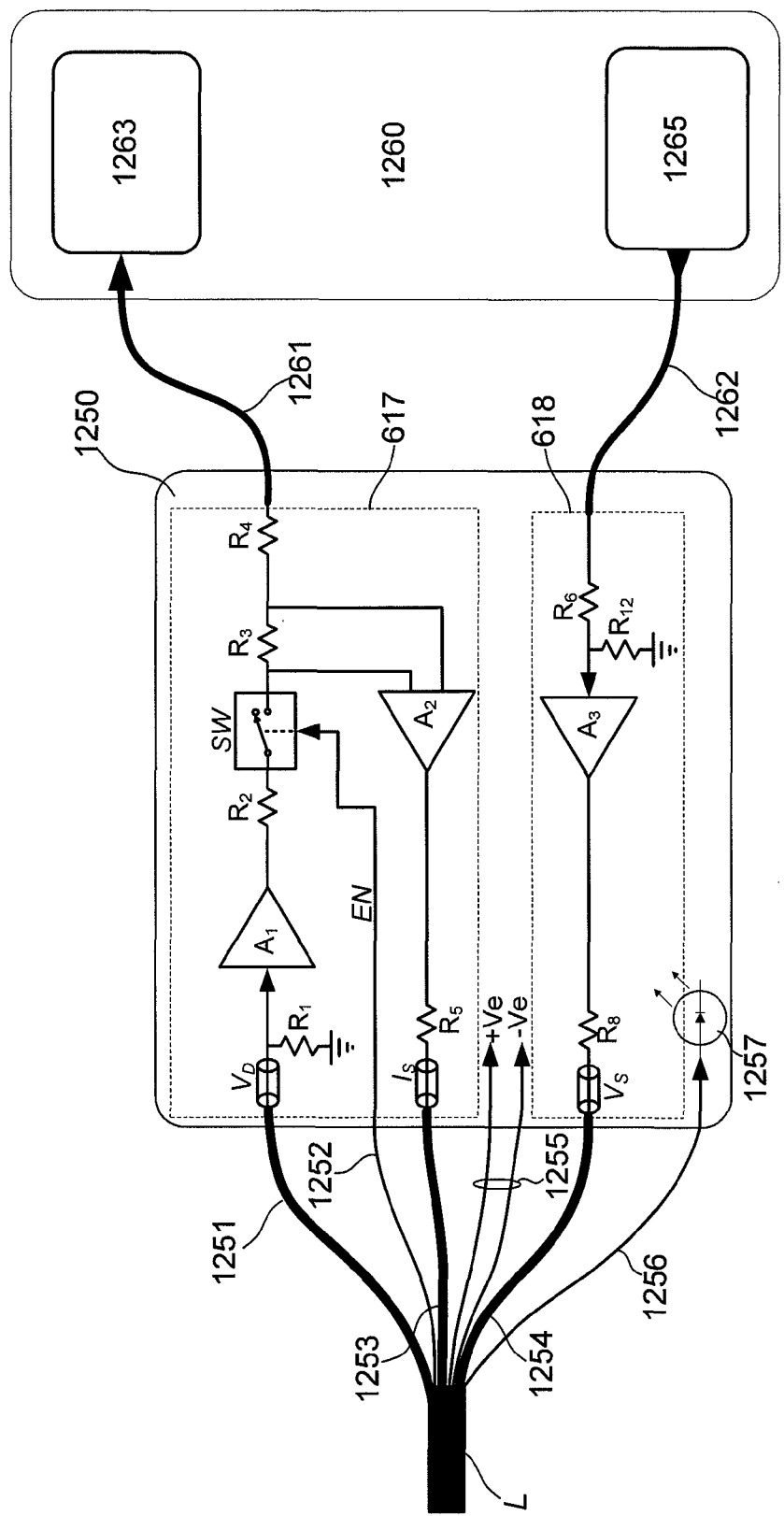
FIG. 12 is a schematic diagram of an example of an electrode system incorporating a signal generator and a sensor.

FIG. 12 is an example of an electrode system for a single one of the channels, which incorporates both a drive electrode 613 and sense electrode 615.

The electrode system incorporates a first substrate 1250, such as a printed circuit board (PCB), or the like, having the respective signal generator 617 and sensor 618 mounted thereon. The general functionality of the signal generator 617 and sensor 618 are represented by the components shown. In practice a greater number of components may be used in a suitable arrangement, as would be appreciated by persons skilled in the art, and the components shown are merely intended to indicate the functionality of the signal generator and the sensor 617, 618.

The substrate 1250 and associated components may be provided in a suitable housing to protect them during use, as will be appreciated by persons skilled in the art.

The signal generator 617 and the sensor 618 are also coupled via respective cables 1261, 1262 to conductive pads 1263, 1265, which may be mounted on a second substrate 1260, and which form the first and second electrodes 613, 615, respectively. It will be appreciated that in use, the cables 1261, 1262 may include clips or the like, to allow the conductive pads to be easily replaced after use. As will be appreciated, the conductive pads 1263, 1265 are typically formed from a silver pad, having a conductive gel, such as silver/silver chloride gel, thereon. This ensures good electrical contact with the subject S.

The conductive pads 1263, 1265 may be mounted on the substrate 1260, so as to ensure that the conductive pads 1263, 1265 are positioned a set distance apart in use, which can help ensure measurement consistency. Alternatively the conductive pads 1263, 1265 can be provided as separate disposable conductive pads, coupled to the first substrate 260 by cables 1261, 1262. Other suitable arrangements may also be used.

In one example, the substrate 1260 is formed from a material that has a low coefficient of friction and/or is resilient, and/or has curved edges to thereby reduce the chances of injury when the electrodes are coupled to the subject.

In this example, the signal generator 617 includes an amplifier $A_1$ having an input coupled to a cable 1261. The input is also coupled to a reference potential, such as ground, via a resistor $R_1$. An output of the amplifier $A_1$ is connected via a resistor $R_2$, to a switch SW, which is typically a CMOS (complementary metal-oxide semiconductor) switch that is used to enable the voltage source. The switch SW is controlled via enabling signals EN received from the processing system 830 via a cable 1262.

The switch SW is in turn coupled via two resistors $R_3$, $R_4$, arranged in series, and then, via the cable 1261, to the conductive pad 1263. A second amplifier $A_2$ is provided with inputs in parallel with the first of the two series resistor $R_3$ and with an output coupled via a resistor $R_5$, to a cable 1253.

Figure 6:
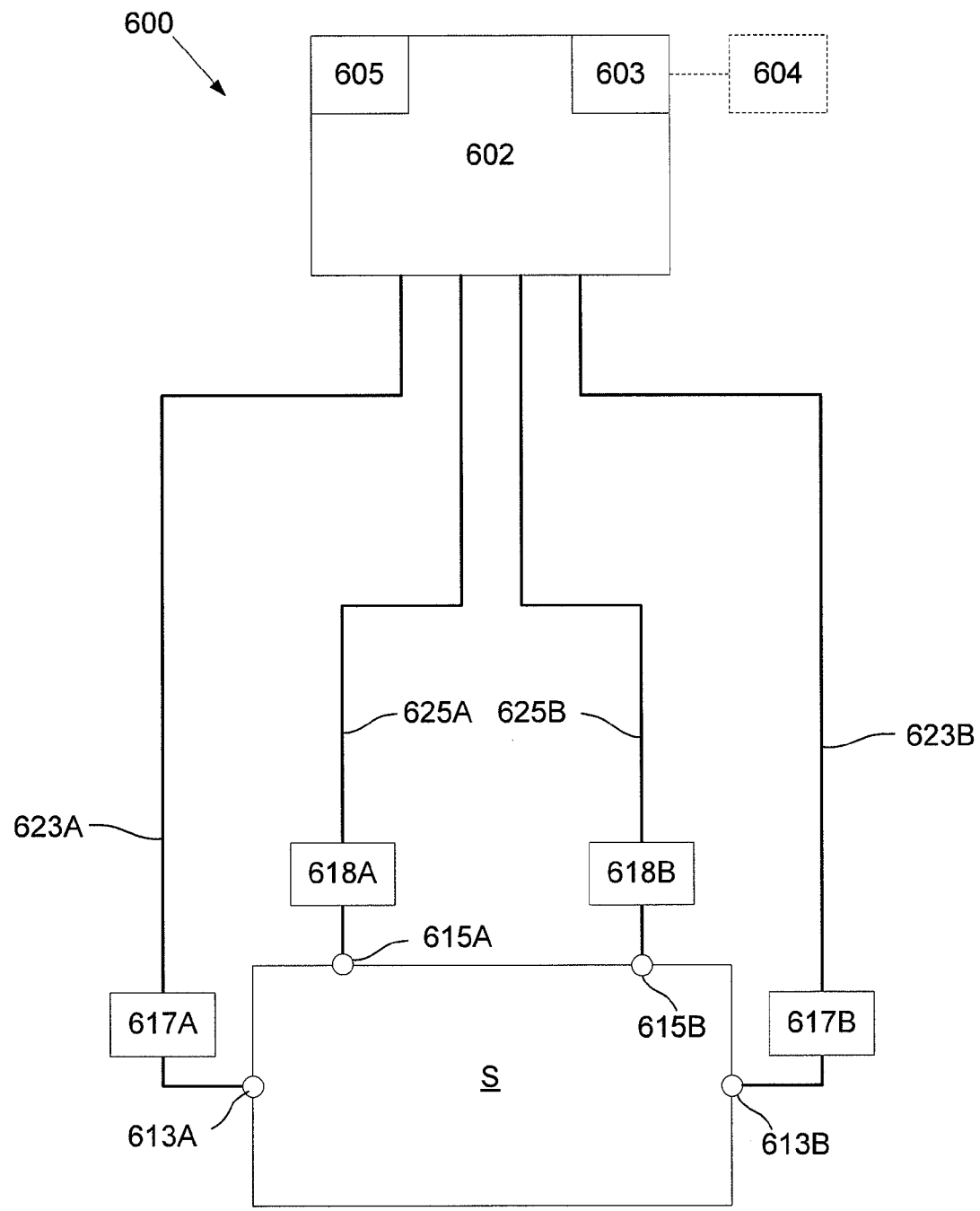
FIG. 6 is a schematic diagram of a third example of impedance measuring apparatus.
Figure 7:
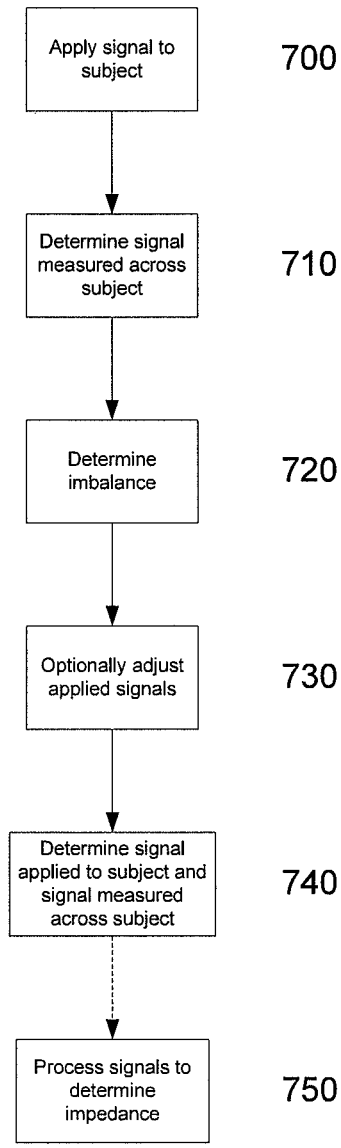
FIG. 7 is a flowchart of an example of a process for performing impedance measuring using the apparatus of FIG. 6.

It will be appreciated from the above that the cables 1251, 1252, 1253 therefore form the lead 623 of FIG. 6. A range of different resistor values may be used, but in one example, the resistors have values of $R_1=R_2=R_5=50\Omega$, and $R_3=R_4=1500\Omega$.

The sensor 618 generally includes an amplifier $A_3$ having an input connected via a resistor $R_6$, and the cable 1262 to the conductive pad 1265. The input is also coupled via a resistor $R_7$, to a reference potential such as a ground. An output of the amplifier $A_3$ is coupled to a cable 1254, via a resistor $R_7$.

It will be appreciated from the above that the cable 1254 therefore forms the lead 625 of FIG. 6. A range of different resistor values may be used, but in one example, the resistors have values of $R_6=1500\Omega$, $R_7=10$ M$\Omega$ and, $R_8=50\Omega$.

Optional power cables 1255 can be provided for supplying power signals +Ve, −Ve, for powering the signal generator 617 and the sensor 618, although alternatively an on board power source such as a battery, may be used. Additionally, a cable 1256 may be provided to allow an LED 1257 to be provided on the substrate 260. This can be controlled by the processing system 830, allowing the operating status of the electrode system to be indicated.

In use, the amplifier $A_1$ operates to amplify the analogue voltage drive signal $V_D$ and apply this to the subject S via the cable 1261, so that the applied potential drives a current through the subject S. It will be appreciated that in use, this will only occur if the switch SW is in a closed position and the switch SW can therefore be placed in an open position to isolate the voltage source from the subject S.

The current of the signal being applied to the subject S is detected and amplified using the amplifier $A_2$, with the amplified current signal $I_S$ being returned to the processing system 830, along the cable 1253 and via the ADC 828.

Similarly, the sensor 618 operates by having the amplifier $A_3$ amplify the potential detected at the second electrode 1256, returning the amplified analogue voltage signal $V_S$ along the cable 1254, to the ADC 827.

The cables 1251, 1252, 1253, 1254, 1255, 1256 may be provided in a number of different configurations depending on the preferred implementation. In one example, each of the cables 1251, 1252, 1253, 1254, 1255, 1256 are provided in a single lead L, although this is not essential, and the cables could be provided in multiple leads.

As briefly mentioned above, when separate leads 623, 625, are used for the voltage signal $V_S$ and the current signal $I_S$, then inductive coupling between the leads 623, 625 can result in EMFs being induced within the leads 623, 625. The magnitude of the EMF is dependent on the degree of coupling between the leads 623, 625 and hence their physical separation, and also increases in proportion to the frequency and amplitude of the current signal $I_S$.

The EMF induced within the leads 623, 625 results in an effective EMF across the input of the sensor 618. As a result, a component of the sensed voltage signal $V_S$ is due, to the induced EMF, which in turn leads to inaccuracies in the determined voltage signal $V_S$ and the current signal $I_S$.

The effect of inductive coupling varies depending on the physical separation of the leads 623, 625. Accordingly, in one example, the effect of inductive coupling between leads can be reduced by physically separating the leads as much as possible. Thus, in one example, the cables 1251, 1252, 1253, 1254, 1255, 1256 are provided in separate physically separated leads. However, a problem with this arrangement is that the amount of inductive coupling will vary depending on the physical lead geometry, which can therefore vary between measurements. As a result, the magnitude of any inductive coupling can vary, making this difficult to account for when analysing the impedance measurements.

An alternative to using physically separate leads for each of the cables 1251, 1252, 1253, 1254, 1255, 1256 is to use a single combined lead L. The lead is formed so that the cables 1251, 1252, 1253, 1254, 1255, 1256 are held in a substantially constant relative physical configuration. In one example, the leads L are formed so as to provide a constant geometric arrangement by twisting each of the respective cables together. However, alternative fabrication techniques could be used such as making the leads from separate un-insulated shielded cables that are over moulded to maintain close contact.

As a result of the constant physical geometry, any EMF induced along the leads 623, 625 is substantially constant, allowing this to be accounted for during a calibration process.

Accordingly, when the measuring device 820 is initially configured, and in particular, when the algorithms are generated for analysing the voltage and current signals $V_S$, $I_S$, to determine impedance measurements, these can include factors that take into account the induced EMF. In particular, during the configuration process, a measuring device 820 can be used to take measurements from reference impedances, with the resulting calculations being used to determine the effect of the induced EMF, allowing this to be subtracted from future measurements.

A further source of errors can be caused by variations in the behavioural response of circuitry and other components used in the electrode system. For example, although similar components would be used on the electrode systems, manufacturing tolerances associated with the components, can mean that the components would exhibit different response to each other under the same external conditions. It will also be appreciated that the degree of variation may depend on the frequency at which a particular measurement is made.

Again however, any such variations can be accounted for during a calibration process by recording measurements from reference impedances over a number of different frequencies.

To allow the results of any such calibration to be taken into account during use, it can be useful to record the results of the calibration in such a manner as to allow these to be accessed by the measuring device 600 in use. This can be achieved in any one of a number of manners.

Thus, for example, each lead set formed from the leads and electrode system, could have a respective identifier. A set of calibration data, indicative of deviations between the response of the lead set and an expected or idealised lead set can then be stored associated with the respective identifier. When the lead set is used with a measuring device 600, the measuring device 600 can determine the lead set identifier, either by way of manually input by an operator, or by automated detection of a suitable identifier provided as part of the electrode system. This then allows the measuring device 600 to access calibration data, which could therefore be stored separately to the measuring device 600, for example on a remote server.

As an alternative however, the calibration data could be stored on the electrode system itself, for example using a suitable memory, such as a EEPROM or the like. In this instance, an additional connection would be provided between the measuring device 600 and the electrode system, thereby allowing the measuring device to poll the memory, and retrieve the calibration data stored thereon. This would in turn allow the calibration data to be taken into account when performing measurements.

Figure 13:
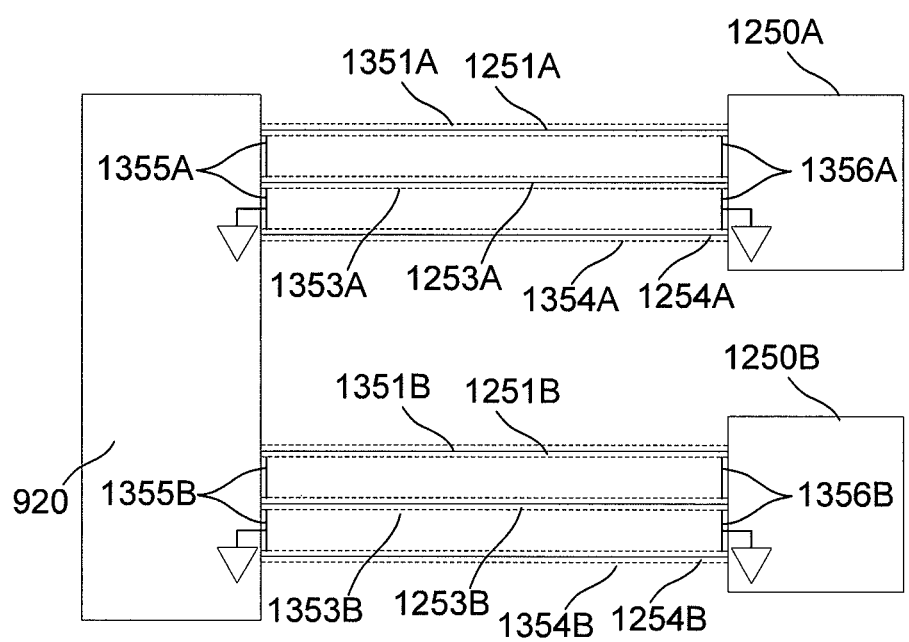
FIG. 13 is a schematic diagram of an example of lead connections between the measuring device and the electrode system of FIG. 12; and, FIG. 14 is a schematic diagram of an example of a lead arrangement.

A further issue with the lead arrangement is that of capacitive coupling between the respective cables, as will now be described with respect to FIG. 13. For the purpose of this example, only cables 1251, 1253, 1254 are shown for clarity.

In this example, the measuring device 820 is connected to the PCB's 1250A, 1250B to provide connections for each of the electrodes 613A, 613B, 615A, 615B. As also shown each of the cables 1251, 1253, 1254 have respective shielding 1351, 1353, 1354 provided thereon. The shielding is used to help prevent coupling between the respective cables 1251, 1253, 1254. It will therefore be appreciated that the cables 1251, 1253, 1254 are generally formed from a shielded wire core. In practice, the shielded cables may be 50Ω transmission lines, which minimize signal transmission distortion at high frequencies, thereby minimizing errors. In addition to this, the shields 1351, 1353, 1354 are typically interconnected at each end, to a reference potential such as a ground, via respective connections 1355, 1356.

The use of shielded and grounded cables in this fashion helps reduce the effect of capacitive coupling, helping to further reduce inaccuracies in obtained measurements.

Figure 14:
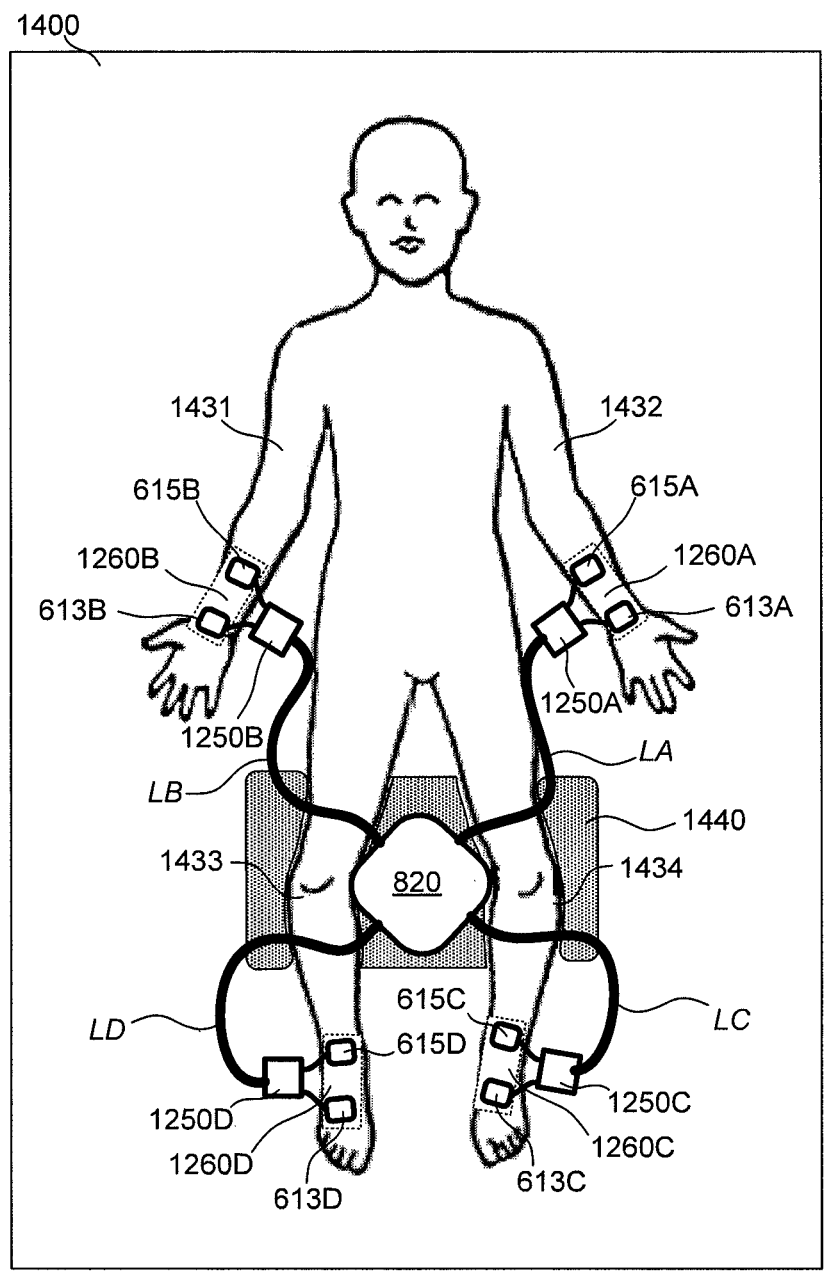

A further potential issue is that of inductive coupling between the different leads L, as well as capacitive coupling between the subject and the subject and the bed. In this regard, parasitic capacitances allow high frequency currents to bypass the intended current path through the body, resulting in measurement errors. To take this into account, in one example, the leads L for each electrode system can be physically separated as much as possible and/or provided in an arrangement that minimises lead length in use. An example of an arrangement for achieving this will now be described with respect to FIG. 14.

For the purpose of this example, the measuring system provides four measuring channels, designated by the suffixes A, B, C, D. It will be appreciated that this can be achieved by using a modified version of the measuring device 820 of FIG. 8, in which further ADCs 827, 828 and DACs 829 are provided as briefly described above.

In this example, the subject S is laying on a bed 1400, with arms 1431, 1432 positioned by the subject's side, and the legs 1433, 1434 resting on a support 1440, which incorporates the measuring device 820. The support 940 may be any form of support, but is typically formed from moulded foam, or the like, which arranges the subjects with the measuring device 820 positioned substantially between the subject's knees. The measuring device 820 is typically incorporated into the support both to ensure accurate location of the subject relative to the measuring device 820, and also to protect the subject S from damage caused by rubbing or other impact with a housing of the measuring device 820.

By providing a four channel arrangement, this allows a respective electrode system to be mounted to each of the subject's limbs. Thus, as shown, each limb 1431, 1432, 1433, 1434 has a respective substrate 1260 mounted thereon, to thereby provide a drive and sense electrode 613, 615 on each wrist and ankle. The electrodes 613, 615, are coupled to respective signal generators and sensors mounted on the substrates 1250, which are in turn coupled to the measuring device 820 via respective leads LA, LB, LC, LD.

The leads are arranged so that each lead LA, LB, LC, LD extends away from the measuring device 820 in different directions, thereby maximizing the physical separation of the leads and hence helping to reduce any inductive coupling therebetween.

Additionally, the leads LA, LB, LC, LD are preferably adapted to extend perpendicularly from both the measuring device 820 and the subject S, to thereby further reduce the effects of capacitive coupling.

Furthermore, by having the measuring device 820 positioned near the subject's knee, this places the measuring device 820 approximately equi-distant between the subject's knees and ankles.

Thus, by arranging the measuring device 820 towards the lower end of the bed 900, this reduces the length of leads LA, LB, LC, LD needed to place the electrodes on the wrist and ankle of the subject S, whilst maintaining substantially equal lead lengths which helps further reduce both inductive and capacitive coupling effects. In this regard, the EMF originating from any inductive coupling effect is proportional to the relevant lead length. Similarly, capacitive coupling between the leads (ground) and the subject S, which can create current shunt paths, is also minimized.

It will be appreciated that in this arrangement, by having four first electrodes and four second electrodes positioned on the limbs, this allows a range of different limb and/or whole body impedance measurements to be performed as described above.

During the measurement procedure, in general only two of the channels will be used at any one time. To achieve this, the other channels will be disabled through use of the respective switch SW, which forms part of the electrode system.

It will be appreciated that the above described impedance measurement apparatus and method variations described above with respect to FIGS. 6 to 14 could be utilised in conjunction with the apparatus and methods of FIGS. 1 to 5 to provide further enhanced measurements. In this arrangement, the techniques used in any one or more of FIGS. 6 to 14 are implemented together with the switch 135, 136, to allow inductive coupling between the leads to also be taken into account using the switching technique. Thus, for example, the lead geometry of FIG. 14 can be used to minimise inductive coupling between the leads, with any residual effect being account for using the process described in FIGS. 1 to 5. Similarly the system can operate to minimise any imbalance using the process of FIG. 7, before accounting for inductive coupling using the method of FIG. 2.

Figure 5:
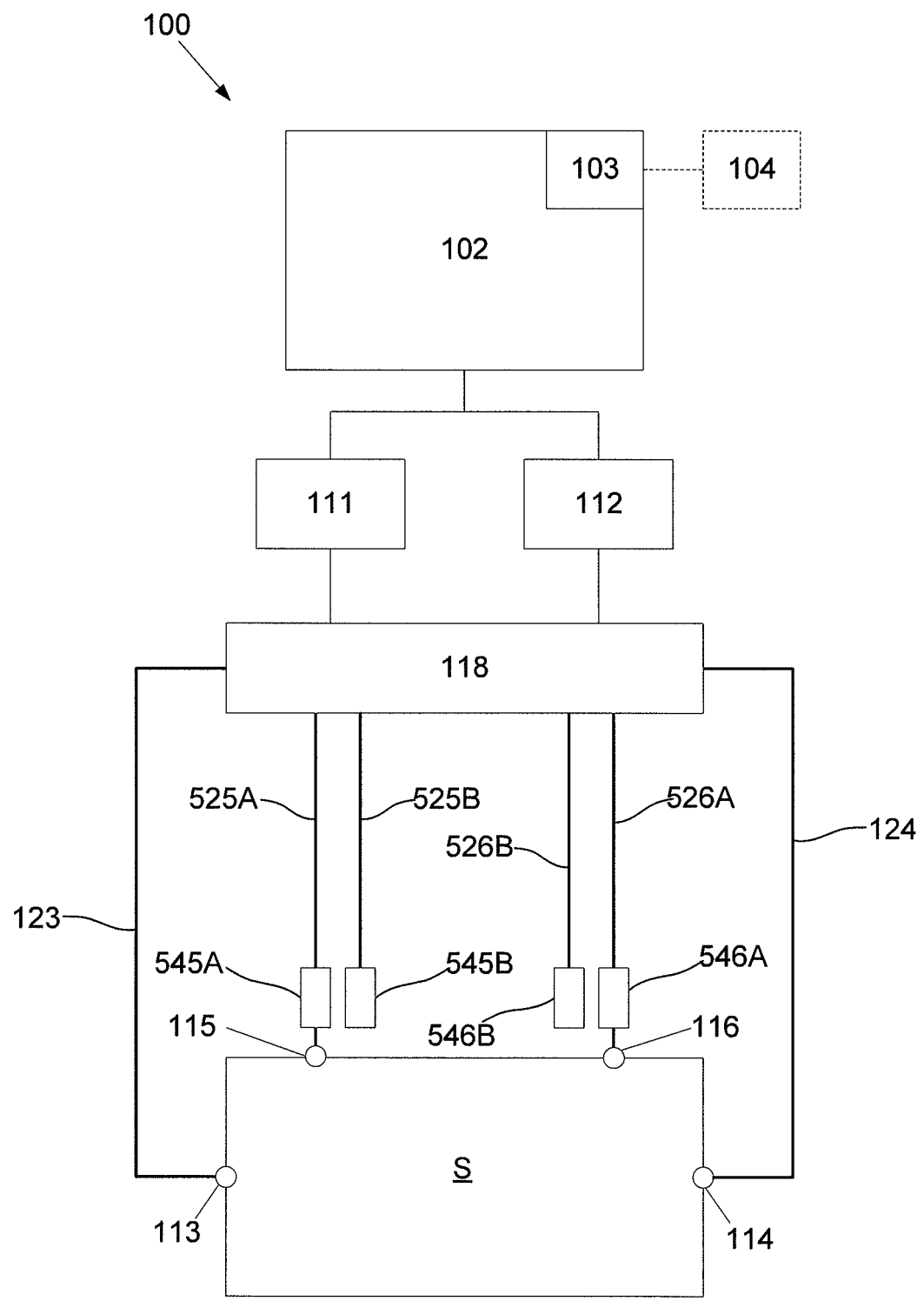
FIG. 5 is a schematic diagram of a second example of impedance measuring apparatus.
Figure 8:
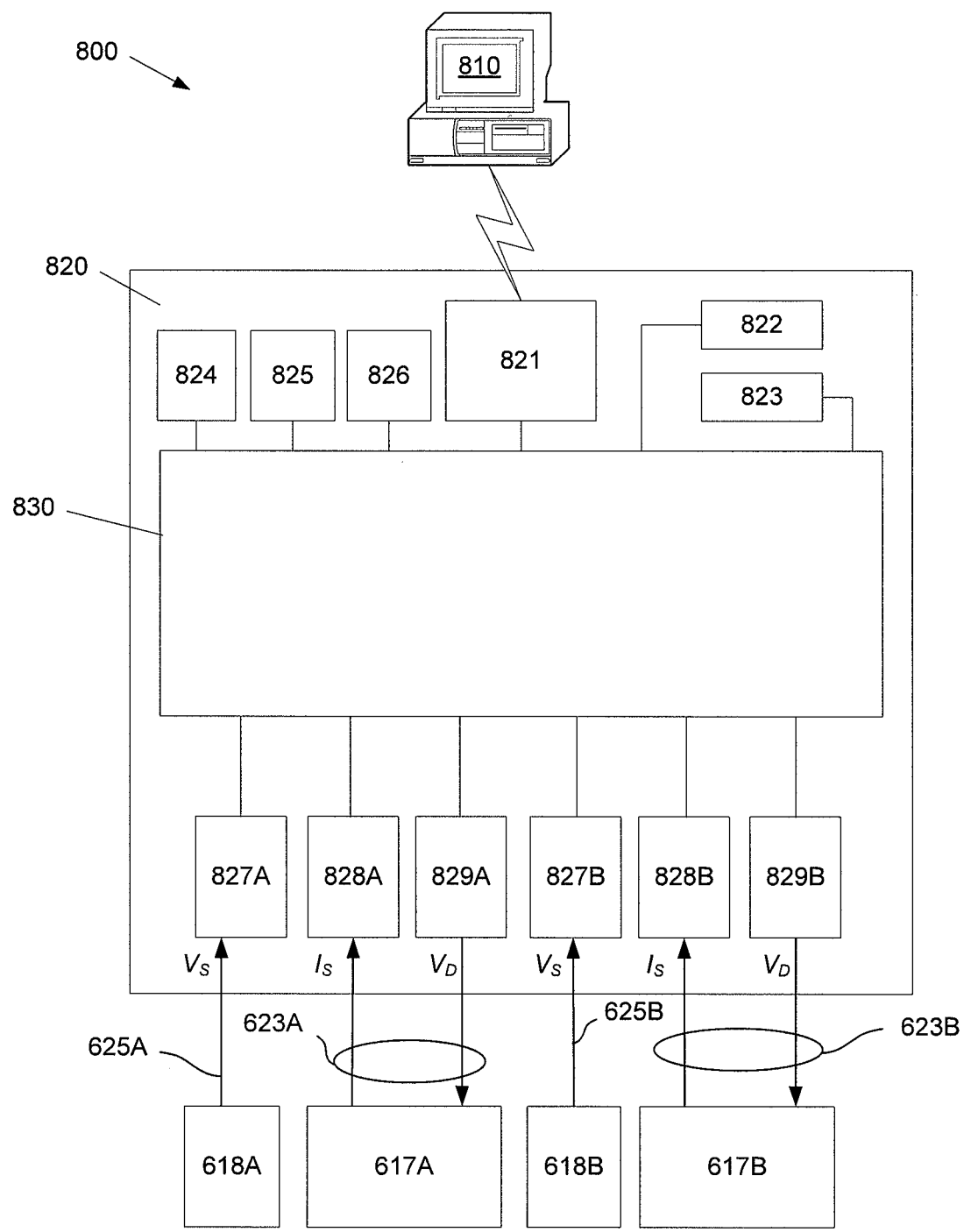
FIG. 8 is a schematic diagram of a fourth example of impedance measuring apparatus.

Similarly, it will be appreciated that the processing system 102 of FIGS. 1 and 5 can be replaced with a separate computer system and processing system, similar to the arrangement of the computer system 810 and processing system 830 of FIG. 8.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used in determining biological indicators, which in turn can be used for diagnosing the presence, absence or degree of a range of conditions and illnesses, including, but not limited to oedema, lymphodema, body composition, as well features of cardiac function, or the like.

Furthermore, whilst the above described examples have focussed on the application of a current signal to allow a voltage to be measured, this is not essential and the process can also be used when applying a voltage signal to allow a current to be sensed.

The invention claimed is:

1. A method for performing impedance measurements on a subject, the method including, in a processing system:
 a) causing at least one electrical signal to be applied to the subject via first leads operatively connected to first electrodes provided on the subject;
 b) determining a first indication indicative of at least one first electrical signal measured via second leads operatively disconnected from second electrodes positioned on the subject while the at least one electrical signal is applied to the subject via first leads;
 c) determining a second indication indicative of at least one second electrical signal measured via second leads operatively connected to second electrodes positioned on the subject while the at least one electrical signal is applied to the subject via first leads; and,
 d) determining from the indications and the at least one applied signal, at least one instantaneous impedance value.

2. A method according to claim 1, wherein the second leads are connected to the second electrodes via respective switches, and wherein the method includes, in the processing system, causing the switches to be selectively opened and closed to allow the first and second indications to be determined.

3. A method according to claim 2, wherein the method includes, in the processing system:
 a) opening the switches;
 b) determining the first indication;
 c) closing the switches; and,
 d) determining the second indication.

4. A method according to claim 1, wherein each second lead includes a lead pair, and wherein each lead pair includes a lead operatively connected to the second electrodes and a lead operatively disconnected to the second electrodes, and wherein the method includes, in the processing system:
 a) determining the first indication using the lead operatively disconnected to the second electrodes; and,
 b) determining the second indication using the lead operatively connected to the second electrodes.

5. A method according to claim 1, wherein the method includes, in the processing system:
 a) determining a number of frequencies;
 b) selecting a next frequency from the number of frequencies;
 c) causing the at least one electrical signal to be applied to the subject at the selected frequency;
 d) determining the first and second indications; and,
 e) repeating steps (b), (c) and (d) for each of the number of frequencies.

6. A method according to claim 5, wherein the method includes, in the processing system:
 a) determining at least one impedance measurement to be performed; and,
 b) determining the number of frequencies using the determined impedance measurement.

7. A method according to claim 5, wherein the method includes, in the processing system:
 a) determining an indication of the at least one signal applied to the subject; and,
 b) determining the at least one instantaneous impedance value using the determined indication.

8. A method according to claim 1, wherein the method includes, in the processing system:

a) modifying the second indication using the first indication; and,
b) using the modified second indication to determine the at least one instantaneous impedance value.

9. A method according to claim 1, wherein the method includes, in the processing system:
   a) determining at least one first instantaneous impedance value using the first indication;
   b) determining at least one second instantaneous impedance value using the second indication; and,
   c) determining the at least one instantaneous impedance value using the first and second instantaneous impedance values.

10. A method according to claim 1, wherein the method includes, in the processing system, using the first and second indications to account for inductive coupling between the first and second leads.

11. Apparatus for performing impedance measurements on a subject, the apparatus including, a processing system for:
   a) causing at least one electrical signal to be applied to the subject via first leads operatively connected to first electrodes provided on the subject;
   b) determining a first indication indicative of at least one first electrical signal measured via second leads operatively disconnected from second electrodes positioned on the subject while the at least one electrical signal is applied to the subject via first leads;
   c) determining a second indication indicative of at least one second electrical signal measured via second leads operatively connected to second electrodes positioned on the subject while the at least one electrical signal is applied to the subject via first leads; and,
   d) determining from the indications and the at least one applied signal, at least one instantaneous impedance value.

12. Apparatus according to claim 11, wherein the apparatus includes switches for selectively operatively connecting the second electrodes to the second leads.

13. Apparatus according to claim 11, wherein the processing system is for opening and closing the switches to thereby selectively operatively connect the second electrodes to the second leads.

14. Apparatus according to claim 11, wherein the apparatus includes buffer circuits for coupling the second leads to the second electrodes.

15. Apparatus according to claim 14, wherein the apparatus includes switches positioned between the buffer circuits and the second electrodes for selectively operatively connecting the second leads to the second electrodes.

16. Apparatus according to claim 11, wherein each second lead includes a lead pair, and wherein each lead pair includes a lead operatively connected to the second electrodes and a lead operatively disconnected to the second electrodes.

17. A method for use in diagnosing the presence, absence or degree of oedema, wherein the method includes:
   a) causing at least one electrical signal to be applied to the subject via first leads operatively connected to first electrodes provided on the subject;
   b) determining a first indication indicative of at least one first electrical signal measured via second leads operatively disconnected from second electrodes positioned on the subject while the at least one electrical signal is applied to the subject via first leads;
   c) determining a second indication indicative of at least one second electrical signal measured via second leads operatively connected to second electrodes positioned on the subject while the at least one electrical signal is applied to the subject via first leads; and,
   d) determining from the indications and the at least one applied signal, at least one instantaneous impedance value.

18. Apparatus for use in diagnosing the presence, absence or degree of oedema, wherein the apparatus includes a processing system for:
   a) causing at least one electrical signal to be applied to the subject via first leads operatively connected to first electrodes provided on the subject;
   b) determining a first indication indicative of at least one first electrical signal measured via second leads operatively disconnected from second electrodes positioned on the subject while the at least one electrical signal is applied to the subject via first leads;
   c) determining a second indication indicative of at least one second electrical signal measured via second leads operatively connected to second electrodes positioned on the subject while the at least one electrical signal is applied to the subject via first leads; and,
   d) determining from the indications and the at least one applied signal, at least one instantaneous impedance value.

19. A method for use in determining body composition, wherein the method includes:
   a) causing at least one electrical signal to be applied to the subject via first leads operatively connected to first electrodes provided on the subject;
   b) determining a first indication indicative of at least one first electrical signal measured via second leads operatively disconnected from second electrodes positioned on the subject while the at least one electrical signal is applied to the subject via first leads;
   c) determining a second indication indicative of at least one second electrical signal measured via second leads operatively connected to second electrodes positioned on the subject while the at least one electrical signal is applied to the subject via first leads; and,
   d) determining from the indications and the at least one applied signal, at least one instantaneous impedance value.

20. Apparatus for use in determining body composition, wherein the apparatus includes a processing system for:
   a) causing at least one electrical signal to be applied to the subject via first leads operatively connected to first electrodes provided on the subject;
   b) determining a first indication indicative of at least one first electrical signal measured via second leads operatively disconnected from second electrodes positioned on the subject while the at least one electrical signal is applied to the subject via first leads;
   c) determining a second indication indicative of at least one second electrical signal measured via second leads operatively connected to second electrodes positioned on the subject while the at least one electrical signal is applied to the subject via first leads; and,
   d) determining from the indications and the at least one applied signal, at least one instantaneous impedance value.

* * * * *

UNITED STATES PATENT AND TRADEMARK OFFICE
CERTIFICATE OF CORRECTION

PATENT NO. : 8,594,781 B2  
APPLICATION NO. : 12/523159  
DATED : November 26, 2013  
INVENTOR(S) : Scott Chetham Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this
Twenty-second Day of September, 2015

Michelle K. Lee
*Director of the United States Patent and Trademark Office*